(12) United States Patent
Xu

(10) Patent No.: US 10,388,898 B2
(45) Date of Patent: Aug. 20, 2019

(54) DOPED PEROVSKITE HAVING IMPROVED STABILITY, AND SOLAR CELLS MADE THEREOF

(71) Applicant: Tao Xu, Lisle, IL (US)

(72) Inventor: Tao Xu, Lisle, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 0 days.

(21) Appl. No.: 15/614,438

(22) Filed: Jun. 5, 2017

(65) Prior Publication Data

US 2018/0350527 A1 Dec. 6, 2018

(51) Int. Cl.
| | |
|---|---|
| *C07F 7/24* | (2006.01) |
| *H01G 9/20* | (2006.01) |
| *H01L 51/00* | (2006.01) |
| *H01L 51/42* | (2006.01) |

(52) U.S. Cl.
CPC ............ *H01L 51/4213* (2013.01); *C07F 7/24* (2013.01); *H01G 9/2009* (2013.01); *H01L 51/0077* (2013.01); *H01G 9/20* (2013.01); *Y02E 10/549* (2013.01)

(58) Field of Classification Search
CPC ............ H01L 51/0077; H01L 51/4213; H01G 9/2009; H01G 9/20; Y02E 10/50; Y02E 10/549; C07F 7/24
See application file for complete search history.

(56) References Cited

U.S. PATENT DOCUMENTS

| | | |
|---|---|---|
| 2011/0220192 A1 | 9/2011 | Tajabadi et al. |
| 2013/0025681 A1 | 1/2013 | Kang et al. |
| 2014/0332078 A1 | 11/2014 | Guo et al. |
| 2015/0129034 A1 | 5/2015 | Snaith |
| 2015/0200377 A1 | 7/2015 | Etgar |
| 2017/0330693 A1* | 11/2017 | Lunt, III .............. H01G 9/2013 |
| 2018/0108491 A1 | 4/2018 | Xu |

FOREIGN PATENT DOCUMENTS

| | | |
|---|---|---|
| CN | 105047826 A  * | 11/2015 |
| EP | 2 693 503 | 2/2014 |
| WO | 2016/163985 | 10/2016 |

OTHER PUBLICATIONS

English machine translation of CN105047826. (Year: 2015).*
Liu, M. et al., "Efficient planar heterojunction perovskite solar cells by vapour deposition", Nature, vol. 501, pp. 395-398, (2013).
Burschka, J. et al., "Sequential deposition as a route to high-performance perovskite-sensitized solar cells", Nature, vol. 499, pp. 316-320, (2013).

(Continued)

*Primary Examiner* — Lindsey A Bernier
(74) *Attorney, Agent, or Firm* — Evan Law Group LLC

(57) ABSTRACT

A light-harvesting material comprises a perovskite absorber doped with a metal chalcogenide. The light-harvesting material may be used in a photovoltaic device, comprising (1) a first conductive layer, (2) an optional blocking layer, on the first conductive layer, (3) a semiconductor layer, on the first conductive layer, (4) a light-harvesting material, on the semiconductor layer, (5) a hole transport material, on the light-harvesting material, and (6) a second conductive layer, on the hole transport material.

13 Claims, 16 Drawing Sheets

(56) References Cited

OTHER PUBLICATIONS

Kazim, S. et al., "Perovskite as light harvester: A game changer in photovoltaics", Angewandte Chemie International Edition, vol. 53, pp. 2812-2824, (2014).
Stranks, S.D. et al., "Electron-hole diffusion lengths exceeding 1 micrometer in an organometal trihalide perovskite absorber", Science, vol. 342, pp. 341-344, (2013).
Leijtens, T. et al., "Overcoming ultraviolet light instability of sensitized $TiO_2$ with meso-superstructured organometal tri-halide perovskite solar cells", Nature Communications, vol. 4, pp. 1-8, (2013).
Hao, F. et al., "Lead-free solid-state organic-inorganic halide perovskite solar cells", Nature Photonics, vol. 8, pp. 489-494, (2014).
Qin, P. et al., "Inorganic hole conductor-based lead halide perovskite solar cells with 12.4% conversion efficiency", Nature Communications, vol. 5, pp. 1-6, (2014).
Christians, J.A. et al., "An inorganic hole conductor for organo-lead halide perovskite solar cells improved hole conductivity with copper iodide", Journal of the American Chemical Society vol. 136, pp. 758-764, (2014).
Li, H. et al., "A simple 3,4-ethylenedioxythiophene based hole-transporting material for perovskite solar cells", Angewandte Chemie International Edition, vol. 53, pp. 4085-4088, (2014).
Zhu, Z. et al., "Efficiency enhancement of perovskite solar cells through fast electron extraction: The role of graphene quantum dots", Journal of American Chemical Society, vol. 136, pp. 3760-3763, (2014).
Ku, Z. et al., "Full printable processed mesoscopic $CH_3NH_3PbI_3$/$TiO_2$ heterojunction solar cells with carbon counter electrode", Scientific Reports, vol. 3, pp. 1-5, (2013).
Lide, D.R. "Handbook on Chemistry and Physics", 88th ed., CRC: Boca Raton, FL, p. 2640, (2008).
Feng, X. et al., "Rapid charge transport in dye-sensitized solar cells made from vertically aligned single-crystal rutile $TiO_2$ nanowires", Angewandte Chemie International Edition, vol. 51, pp. 2727-2730, (2012).
Etgar, L. et al., "Mesoscopic $CH_3NH_3PbI_3$ /$TiO_2$ heterojunction solar cells", Journal of the American Chemical Society, vol. 134, pp. 17396-17399, (2012).
Zhao, Y. et al., "Charge transport and recombination in perovskite ($CH_3$ $NH_3$)$PbI_3$ sensitized $TiO_2$ solar cells", Journal of Physical Chemistry Letters, vol. 4, pp. 2880-2884, (2013).
Snaith, H.J. et al., "Anomalous hysteresis in perovskite solar cells", Journal of Physical Chemistry Letters, vol, 5, pp. 1511-1515, (2014).
Dualeh, A. et al., "Impedance spectroscopic analysis of lead iodide perovskite-sensitized solid-state solar cells", ACS Nano, vol. 8, pp. 362-373, (2014).
Green, M.A., "Solar cells: Operating principles, technology and system applications", Prentice-Hall, Inc., pp. 96-97, (1982).
Jiang, Q. et al., "Rutile $TiO_2$ nanowires perovskite solar cells", Electronic Supplementary Information, Chemical Communications, pp. 1-4, (2014).
O'Regan, B.C. et al., "Measuring charge transport from transient photovoltage rise times. A new tool to investigate electron transport in nanoparticle films", Journal of Physical Chemistry B, vol. 110, pp. 17155-17160, (2006).
Jiang, Q. et al., "Nickel-cathoded perovskite solar cells", The Journal of Physical Chemistry C, vol. 118, pp. 25878-25883, with supplemental information, pp. 1-4, (2014).
Jiang, Q. et al., "Rutile $TiO_2$ nanowire-based perovskite solar cells", Chemical Communication, vol. 50, pp. 14720-14723, (2014).
Niu, G. et al., "Study on the stability of $CH_3NH_3PbI_3$ films and the effect of pest-modification by aluminum oxide in all-solid-state hybrid solar cells", Journal of Materials Chemistry A, vol. 2, pp. 705-710, (2014).
Abate, A. et al., "Supramolecular halogen bond passivation of organic-inorganic halide perovskite solar cells", Nano Letters, vol. 14, pp. 3247-3254, (2014).

Yang, J. et al., "Investigation of $CH_3NH_3PbI_3$ degradation rates and mechanisms in controlled humidity environments using in situ techniques", ACS Nano, vol. 9, pp. 1955-1963, (2015).
Chen, Q. et al., "Controllable self-induced passivation of hybrid lead iodide perovskites toward high performance solar cells", Nano Letters, vol. 14, pp. 4158-4163, (2014).
Park, B-W. et al., "Enhanced crystallinity in organic-inorganic lead halide perovskites on mesoporous $TiO_2$ via disorder-order phase transition", Chemistry of Materials, vol. 26, pp. 4466-4471, (2014).
Baikie, T. et al., "Synthesis and crystal chemistry of the hybrid perovskite ($CH_3NH_3$)$PbI_3$ for solid-state sensitized solar cell applications", Journal of Materials Chemistry A, vol. 1, pp. 5628-5641, (2013).
Chiang, C-H. et al., "Bulk heterojunction perovskite-PCBM solar cells with high fill factor", Nature Photonics, vol. 10, pp. 196-200, (2016).
Liu, D. et al., "Perovskite solar cells with a planar heterojunction structure prepared using room-temperature solution processing techniques", Nature Photonics, vol. 8, pp. 133-138, (2014).
Noorden, R.V., "Cheap solar cells tempt businesses: Easy-to-make perovskite films rival silicon for efficiency", Nature, vol. 513, p. 470, (2014).
Jiang, Q. et al., "Pseudohalide-induced moisture tolerance in perovskite $CH_3NH_3Pb(SCN)_2I$ thin films", Angewandte Chemie International Edition, vol. 54, pp. 7617-7620, (2015).
Miyata, A. et al., "Direct measurement of the exciton binding energy and effective masses for charge carriers in an organic-inorganic tri-halide perovskite", Nature Physics, vol. 11, pp. 582-587, (2015).
Chen, Y. et al., "Extended carrier lifetimes and diffusion in hybrid perovskites revealed by hall effect and photoconductivity measurements", Nature Communications, vol. 7, pp. 1-9, (2016).
Shi, D. et al., "Low trap-state density and long carrier diffusion in organolead trihalide perovskite single crystals", Science, vol. 347, issue 6221, pp. 519-522, (2015).
Wehrenfennig, C. et al., "High charge carrier mobilities and lifetimes in organolead trihalide perovskites", Advanced Materials, vol. 26, pp. 1584-1589, (2014).
Bi, Y. et al., "Charge carrier lifetimes exceeding 15 μs in methylammonium lead iodide single crystals", The Journal of Physical Chemistry Letters, vol. 7, pp. 923-928, (2016).
Im, J-H. et al., "Growth of $CH_3NH_3PbI_3$ cuboids with controlled size for high-efficiency perovskite solar cells", Nature Nanotechnology, vol. 9, pp. 927-932, (2014).
Kaltenbrunner, M. et al., "Flexible high power-per-weight perovskite solar cells with chromium oxide-metal contacts for improved stability in air", Nature Materials, vol. 14, pp. 1032-1039, (2015).
Green, M.A. et al., "The emergence of perovskite solar cells", Nature Photonics, vol. 8, pp. 506-514, (2014).
Jeon, N.J. et al., "Solvent engineering for high-performance inorganic-organic hybrid perovskite solar cells", Nature Materials, vol. 13, pp. 897-903, (2014).
Nie, W. et al., "High-efficiency solution-processed perovskite solar cells with millimeter-scale grains", Science, vol. 347, issue 6221, pp. 522-525, (2015).
Chen, W. et al., "Efficient and stable large-area perovskite solar cells with inorganic charge extraction layers", Science, vol. 350, pp. 944-948, (2015).
Noh, J.H. et al., "Chemical management for colorful, efficient, and stable inorganic-organic hybrid nanostructured solar cells", Nano Letters, vol. 13, pp. 1764-1769, (2013).
Zhu, H. et al., "Lead halide perovskite nanowire lasers with low lasing thresholds and high quality factors", Nature Materials, vol. 14, pp. 636-642, (2015).
Fu, Y. et al., "Nanowire lasers of formamidinium lead halide perovskites and their stabilized alloys with improved stability", Nano Letters, vol. 16, pp. 1000-1008, (2016).
Fu, Y. et al., "Broad wavelength tunable robust lasing from single-crystal nanowires of cesium lead halide perovskites ($CsPbX_3$, X=Cl, Br, I)", ACS Nano, vol. 10, pp. 7963-7972, (2016).
Frost, J.M. et al., "Atomistic origins of high-performance in hybrid halide perovskite solar cells", Nano Letters, vol. 14, pp. 2584-2590, (2014).

(56) References Cited

OTHER PUBLICATIONS

Leguy, A.M.A. et al., "The dynamics of methylammonium ions in hybrid organic-inorganic perovskite solar cells", Nature Communications, vol. 6, pp. 1-10, (2015).
You, J. et al., "Improved air stability of perovskite solar cells via solution-processed metal oxide transport layers", Nature Nanotechnology, vol. 11, pp. 75-81, (2016).
Meloni, S. et al., "Ionic polarization-induced current-voltage hysteresis in $CH_3NH_3PbX_3$ perovskite solar cells", Nature Communications, vol. 7, pp. 1-9, (2016).
Frost, J.M. et al., "Molecular ferroelectric contributions to anomalous hysteresis in hybrid perovskite solar cells", APL Materials, vol. 2, pp. 081506-1-081506-10, (2014).
Gratzel, M., "The light and shade of perovskite solar cells", Nature Materials, vol. 13, pp. 838-842, (2014).
Li, X., et al., "Improved performance and stability of perovskite solar cells by crystal crosslinking with alkylphosphonic acid ω-ammonium chlorides", Nature Chemistry, vol. 7, pp. 703-711, (2015).
Binek, A. et al., "Stabilization of the trigonal high-temperature phase of formamidinium lead iodide", The Journal of Physical Chemistry Letters, vol. 6, pp. 1249-1253, (2015).
Tai, Q. et al., "Efficient and stable perovskite solar cells prepared in ambient air irrespective of the humidity", Nature Communications, vol. 7, pp. 1-8, (2016).
Cao, D.H. et al., "2D homologous perovskites as light-absorbing materials for solar cell applications", Journal of the American Chemical Society, vol. 137, pp. 7843-7850, (2015).
Daub, M. et al., "Synthesis, single-crystal structure and characterization of $(CH_3NH_3)_2Pb(SCN)_2I_2$", Angewandte Chemie International Edition, vol. 54, pp. 11016-11017, (2015).
Tsai, H. et al., "High-efficiency two-dimensional ruddlesden-popper perovskite solar cells", Nature, vol. 536, pp. 312-316, (2016).
Xiao, Z. et al., "Photovoltaic properties of two-dimensional $(CH_3NH_3)_2Pb(SCN)_2I_2$ Perovskite: A combined experimental and density functional theory study", The Jornal of Physical Chemistry Letters, vol. 7, pp. 1213-1218, (2016).
Ogomi, Y. et al., "$CH_3NH_3Sn_xPb_{(1-x)}I_3$ perovskite solar cells covering up to 1060 nm", The Journal of Physical Chemistry Letters, vol. 5, pp. 1004-1011, (2014).
Chen, Q. et al., "Under the spotlight: The organic-inorganic hybrid halide perovskite for optoelectronic applications", Nano Today, vol. 10, pp. 355-396, (2015).
Sutter-Fella, C.M. et al., "High photoluminescence quantum yield in band gap tunable bromide containing mixed halide perovskites", Nano Letters, vol. 16, pp. 800-806, (2016).
Yang, M. et al., "Facile fabrication of large-grain $CH_3NH_3PbI_{3-x}Br_x$ films for high-efficiency solar cells via $CH_3NH_3Br$-selective ostwald ripening", Nature Communications, vol. 7, pp. 1-9, (2016).
Zhao, Y. et al., "Efficient planar perovskite solar cells based on 1.8 eV band gap $CH_2NH_3PbI_2Br$ nanosheets via thermal decomposition", Journal of the American Chemical Society, vol. 136, pp. 12241-12244, (2014).
Kong, L. et al., "Simultaneous band-gap narrowing and carrier-lifetime prolongation of organic-inorganic trihalide perovskites", Proceeding of the National Academy of Science, vol. 113, pp. 8910-8915, (2016).
Evers, W.H. et al., "High charge mobility in two-dimensional percolative networks of PbSe quantum dots connected by atomic bonds", Nature Communications, vol. 6, pp. 1-8, (2015).
Miller, E.M. et al., "Revisiting the valence and conduction band size dependence of PbS quantum dot thin films", ACS Nano, vol. 10, pp. 3302-3311, (2016).
Ekuma, C.E. et al., "Optical properties of PbTe and PbSe", Physical Review B, vol. 85, pp. 085205-1-08205-7, (2012).
Zhang, N. et al., "Narrow band gap lead sulfide hole transport layers for quantum dot photovoltaics", Applied Materials & Interfaces, vol. 8, pp. 21417-21422, (2016).
Svane, A. et al., "Quasiparticle self-consistent GW calculations for PbS, PbSe, and PbTe: Band structure and pressure coefficients", Physical Review B, vol. 81, pp. 245120-1-245120-10, (2010).
Primera-Pedrozo, O. et at., "Room temperature synthesis of PbSe quantum dots in aqueous solution: Stabilization by interactions with ligands", Nanoscale, vol. 4, pp. 1312-1320, (2012).
Heo, J.H. et at., "Efficient inorganic-organic hybrid heterojunction solar cells containing perovskite compound and polymeric hole conductors", Nature Photonics, vol. 7, pp. 486-491, (2013).
Eperon, G.E. et al., "Morphological control for high performance, solution-processed planar heterojunction perovskite solar cells", Advanced Functional Materials, vol. 24, pp. 151-157, (2014).
Lee, J-H. et al., "Role of hydrogen-bonding and its interplay with octahedral tilting in $CH_3NH_3PbI_3$", Chemical Communication, vol. 51, pp. 6434-6437, (2015).
Ong, K.P. et al., "Structural evolution in methylammonium lead iodide $CH_3NH_3PbI_3$", The Journal of Physical Chemistry, vol. 119, pp. 11033-11038, (2015).
Stoumpos, C.C. et al., "Semiconducting tin and lead iodide perovskites with organic cations: Phase transitions, high mobilities, and near-infrared photoluminescent properties", Inorganic Chemistry, vol. 52, pp. 9019-9038, (2013).
Navas, J. et al., "New insights into organic-inorganic hybrid perovskite $CH_3NH_3PbI_3$ nanoparticles. An experimental and theoretical study of doping in $Pb^{2+}$ sites with $Sn^{2+}$, $Sr^{2+}$, $Cd^{2+}$ and $Ca^{2+}$" Nanoscale, vol. 7, pp. 6216-6229, (2015).
Li, Z. et al., "Stabilizing perovskite structures by tuning tolerance factor: Formation of formamidinium and cesium lead iodide solid-state alloys", Chemistry of Materials, vol. 28, pp. 284-292, (2016).
Aguiar, J.A. et al., "Effect of water vapor, temperature, and rapid annealing on formamidinium lead triiodide perovskite crystallization", ACS Energy Letters, vol. 1, pp. 155-161, (2016).
Kim, M.K. et al., "Effective control of crystal grain size in $CH_3NH_3Pb_3$ perovskite solar cells with a pseudohalide $Pb(SCN)_2$ additive", CrystEngComm, vol. 18, pp. 6090-6095, (2016).
Gong, J. et al., "Electron-rotor interaction in organic-inorganic lead iodide perovskites discovered by isotope effects", The Journal of Physical Chemistry Letters, vol. 7, pp. 2879-2887, (2016).
Yang, M. et al., "Square-centimeter solution-processed planar $CH_3NH_3PbI_3$ perovskite solar cells with efficiency exceeding 15%", Advanced Materials, vol. 27, pp. 6363-6370, (2015).
Glaser, T. et al., "Infrared spectroscopic study of vibrational modes in methylammonium lead halide perovskites", The Journal of Physical Chemistry Letters, vol. 6, pp. 2913-2918, (2015).
Flender, O. et al., "Ultrafast photoinduced dynamics of the organolead trihalide perovskite $CH_3NH_3Pb_3$ on mesoporous $TiO_2$ scaffolds in the 320-920 nm range", Physical Chemistry Chemical Physics, vol. 17, pp. 19238-19246, (2015).
Fornaro, T. et al., "Hydrogen-bonding effects on infrared spectra from anharmonic computations: Uracil-water complexes and uracil dimers", The Journal of Physical Chemistry A, vol. 119, pp. 4224-4236, (2015).
Al-Adhami, L. et al., "Band-broadening in infra-red spectra of gaseous hydrogen-bonded complexes", Nature, vol. 211, pp. 1291, (1966).
Yang, J-H. et al., "Fast self-diffusion of ions in $CH_3NH_3PbI_3$: the intersticicaly mechanism versus vacancy-assisted mechanism", Journal of Materials Chemistry A, vol. 4, pp. 13105-13112, (2016).
Yang, T-Y. et al., "The significance of ion conduction in a hybrid organic-inorganic lead-iodide-based perovskite photosensitizer", Angewandte Chemie International Edition, vol. 54, pp. 7905-7910, (2015).
Yuan, Y. et al., "Electric-field-driven reversible conversion between methylammonium lead triiodide perovskites and lead iodide at elevated temperatures", Advanced Energy Materials, vol. 6, pp. 1501803-1-1501803-7, (2016).
Freitag, M. et al., "Dye-sensitized solar cells for efficient power generation under ambient lighting", Nature Photonics, vol. 11, pp. 372-379, (2017).
Saparov, B. et al., "Organic-inorganic perovskites: structural versatility for functional materials design", Chemical Reviews, vol. 116, pp. 4558-4596, (2016).
Stoumpos, C.C. et al., "Ruddlesden-popper hybrid lead iodide perovskite 2D homologous semiconductors", Chemistry of Materials, vol. 28, pp. 2852-2867, (2016).

(56) References Cited

OTHER PUBLICATIONS

Tauc, J. et al., "Optical properties and electronic structure of amorphous germanium", Physica Status Solidi, vol. 15, pp. 627-637, (1966).
Tauc, J. "Optical properties of non-crystalline solids", Optical Properties of Solids, Chapter 5, pp. 277-313, (1972).
International Search Report and Written Opinion dated Jul. 9, 2015 for PCT application No. PCT/US2015/24574, 21 pages.
"Perovskite solar cell", Wikipedia, found at https://en.wikipedia.org/wiki/Perovskite_solar_cell, pp. 1-7, printed on Mar. 14, 2015.
Pp. 5, Sep. 28, 2018, U.S. Appl. No. 15/564,950.
Gong, J. et al., "Divalent anionic doping in perovskite solar cells for enhanced chemical stability", Advanced Materials, vol. 30, issue 34, pp. 1800973-1-1800973-6, (2018).
Pp. 22, Dec. 26, 2018, U.S. Appl. No. 15/564,950.

* cited by examiner $CH_3NH_3PbI_3$

0hr

CH$_3$NH$_3$PbI$_3$ 30 min

DOPED PEROVSKITE HAVING IMPROVED STABILITY, AND SOLAR CELLS MADE THEREOF

FEDERALLY SPONSORED RESEARCH OR DEVELOPMENT

This invention was made with government support under CBET-1150617 awarded by the National Science Foundation. The government has certain rights in the invention.

BACKGROUND

Photovoltaic (PV) systems are systems that convert light into electricity. All photovoltaic systems share a few common parts. All photovoltaic systems include light-harvesting function, a charge-separating function, charge-transporting function, and a charge collecting function.

In the past several years, organic-inorganic metal halide perovskites ($ABX_3$, $A=CH_3NH_3^+$, $(NH_2)_2CH^+$, $B=Pb^{2+}$, $Sn^{2+}$, $X=Cl^-$, $Br^-$, $I^-$) have risen to be a class of promising new photovoltaic materials due to their attractive merits, such as solution processability, low cost of material precursors and ease of device fabrication.[1-3] Among the class of hybrid perovskites, methylammonium lead iodide ($CH_3NH_3PbI_3$) represents an outstanding light absorber ($1.5 \times 10^4$/cm at 550 nm)[4,5] with superior photovoltaic properties such as ease of free carrier generations[6], long carrier diffusion lengths[7,8] even with its moderate mobilities,[9] and the surprisingly long carrier lifetimes[7,10], and has attracted extensive attention for its phenomenal photovoltaic performance, as well as other emerging properties including ferroelectrics and nano-lasing.[11-23] Although $CH_3NH_3PbI_3$ owns such prominences, it suffers from several inherent problems, including lead toxicity, current-voltage hysteresis, and low stability in humidity.[24-27] According to perovskite crystal structures and previous studies, the first step of structural degradation due to moisture involves the formation of hydrated $PbX_6^{4-}$ intermediate and removal of the methylammonium from the sub-lattice structure, this produces a large amount of charge imbalance and the resultant self-repelling $PbI_3^-$ lattice collapses to generate $PbI_2$. In order to tackle this problem, modifications of chemical composition in the perovskite active layer have been practiced by introducing dopants and new chemical moieties geared towards moisture tolerance.[4,28,29] Successful examples of enhancing moisture stability of perovskites was previously realized through partially replacing the halides with pseudohalides such as $SCN^-$ or partially replacing the $CH_3NH_3^+$ with butylammonium, so as to convert the three-dimensional perovskite structure to a Ruddlesden-Popper type, two-dimensional perovskite structures.[4,30-33] However, the resulting layered structure hinders charge transport through structurally confining photocarriers in 2-D inorganic sheets of the materials.[33, 34] Thus, it is imperative to explore chemical pathways that retain the 3-dimensionality of the perovskite structure and good photo-absorption while still enhancing the chemical stability of the entire structure to battle the invasion of water molecules.

SUMMARY

In a first aspect, the present invention is a light-harvesting material, comprising a perovskite absorber doped with a metal chalcogenide.

In a second aspect, the light-harvesting material comprises a perovskite absorber. The perovskite absorber has the formula $ABX_3$, A is selected from the group consisting of alkyl ammonium, formamidinium and mixtures thereof, B is selected from the group consisting of lead, tin and mixtures thereof, X is selected from the group consisting of F, Cl, Br, SCN, I and mixtures thereof, the metal of the metal chalcogenide is selected from the group consisting lead, tin and mixtures thereof, and the chalcogenide of the metal chalcogenide is selected from the group consisting S, Se, Te and mixtures thereof. Preferably A comprises methyl ammonium, B comprises lead, X comprises I, and the chalcogenide comprises Se.

In a third aspect the present invention is a photovoltaic device, comprising (1) a first conductive layer, (2) an optional electron blocking layer, on the first conductive layer, (3) a semiconductor layer, on the optional electron blocking layer, (4) a light-harvesting material, on the semiconductor layer, (5) a hole transport material, on the light-harvesting material, and (6) a second conductive layer, on the hole transport material. The light-harvesting material comprises a perovskite absorber doped with a metal chalcogenide.

In a fourth aspect, the present invention is a method of making a perovskite absorber, comprising forming a solution comprising: a first component selected from the group consisting of alkyl ammonium, formamidinium and mixtures thereof, a second component selected from the group consisting of lead, tin, and mixtures thereof, a third component selected from the group consisting of F, Cl, Br, SCN, I and mixtures thereof, and a fourth component selected from S, Se, Te or mixtures thereof, and forming the perovskite absorber from the solution. The perovskite absorber is doped with a metal chalcogenide.

DEFINITIONS

A "perovskite solar cell" or "perovskite-type solar cell" is a solar cell which includes a perovskite absorber as the light-harvesting element.

A "perovskite absorber" is a compound of formula $ABX_3$, where A is a metal atom such as lead or tin, B is a counter ion (typically an alkyl ammonium compound), and X is a halide (F, Cl, Br, or I) or pseudohalide (such as SCN), which forms crystals of the perovskite structure. Examples include $CH_3NH_3PbX_3$ (3-dimensional perovskite) and $H_2NCHNH_2PbX_3$ (3-dimensional perovskite) and $CH_3NH_3Pb(SCN)_2I$ (Ruddlesden-Popper type). Examples of structure which are perovskite structures included 3-dimensional perovskite, Ruddlesden-Popper type and Dion-Jacobson type. In some cases, the perovskite absorber is doped, which may result in additional atoms located in interstitial sites and/or the formation of vacancies. Examples of a perovskite absorber that is doped included $CH_3NH_3PbI_3$:10% PbSe, which is $CH_3NH_3PbI_3$ doped with 10% PbSe, and therefore the stoichiometry may deviate from the $ABX_3$ formula.

All percentages are weight/weight (w/w) percentages, unless indicated otherwise.

DETAILED DESCRIPTION

Figure 1:
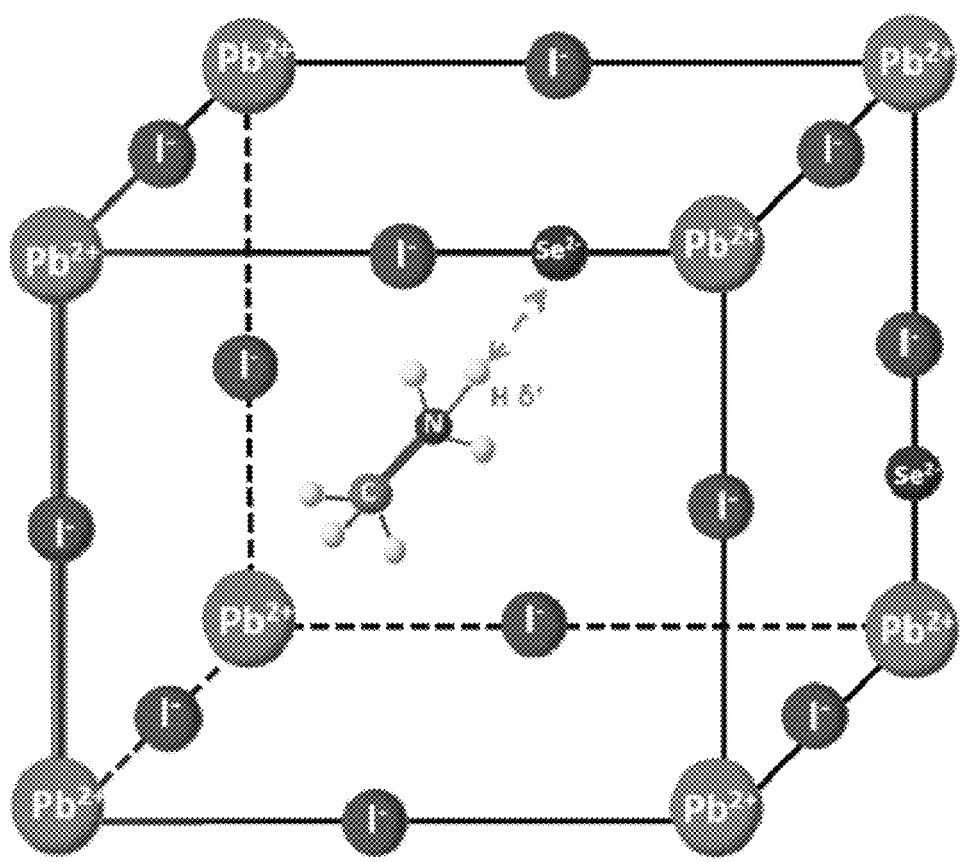
FIG. 1 shows a schematic depiction of the hypothesized PbSe doped $CH_3NH_3PbI_3$ lattice structure.

The present invention includes a light-harvesting material comprising a perovskite absorber and a dopant to increase the stability of the light-harvesting material to moisture. Preferably the perovskite absorber is an organic-inorganic metal halide (or pseudohalide) perovskite, and the dopant is a metal chalcogenide.

A "perovskite absorber" is a compound of formula $ABX_3$, where A is a metal atom such as lead or tin, B is a counter ion (typically an alkyl ammonium compound), and X is a halide (F, Cl, Br, or I) or pseudohalide (such as SCN, SeCN), which forms crystals of the perovskite structure. Examples include $CH_3NH_3PbX_3$ (3-dimensional perovskite) and $H_2NCHNH_2PbX_3$ (3-dimensional perovskite) and CH3NH3Pb(SCN)2I (Ruddlesden-Popper type). Examples of structure which are perovskite structures included 3-dimensional perovskite, Ruddlesden-Popper type and Dion-Jacobson type. In some cases, the perovskite absorber is doped, which may result in additional atoms located in interstitial sites and/or the formation of vacancies. Examples of a perovskite absorber that is doped included CH3NH3PbI3:10% PbSe, which is $CH_3NH_3PbI_3$ doped with 10% PbSe, and therefore the stoichiometry may deviate from the $ABX_3$ formula.

$CH_3NH_3PbI_3$ is known as an outstanding light absorber, but it is also known to have low stability in humidity. The present application demonstrates that by doping $Se^{2-}$ in the form of PbSe into $CH_3NH_3PbI_3$ lattice, the moisture stability of perovskite remarkably, can be enhanced 200 fold, as signified by evolution of optical reflectance. Meanwhile, a phenomenal 10.4% power conversion efficiency was achieved.

The dopant may be present in an amount of 5 to 20% by weight of the light-harvesting material. At higher concentrations, it is possible that phase separation may begin to occur between the dopant and the perovskite absorber. Preferably the dopant is present in an amount of 7 to 12% by weight, most preferably 9 to 11% by weight.

The doped films of PbSe doped $CH_3NH_3PbI_3$ exhibited over two-hundred-fold improved stabilities as compared to conventional $CH_3NH_3PbI_3$ film, which degraded in half an hour in 100% humid environment. Powder diffraction and IR studies of 10% w/w PbSe doped $CH_3NH_3PbI_3$ confirms that an increase in the cubic nature of the perovskite lattice, with a decrease in tetragonal/octahedral nature, the presence of hydrogen-bonding like interactions, and the covalence of the perovskite lattice, which may contribute to the overall stability of organic-inorganic perovskite. The increase in the cubic nature appears to increase moisture resistance.

From the viewpoint of fundamental coordination chemistry, anions with a less electronegative nature (such as $I^-$ vs $Br^-$ and $Cl^-$) are capable of forming chemical bonds with $Pb^{2+}$ which are more covalent, thus favoring charge generation and hole transport.[35,36] On the other hand, weak electronegativity in anions leads to weak attraction between the anionic framework and the organic cations, thus deteriorating the chemical stability. This is evident by the fact that doping $Br^-$ helps the stability of the perovskite structure, but at the cost of greatly narrowed absorption in the visible spectrum (from 775 nm to 540 nm as upper limit).[37-39]

A higher order anionic charge should greatly increase such electrostatic interaction, in comparison to a monovalent halide, so as to stabilize $CH_3NH_3^+$ from moisture solvation.[40] Such electron-rich environments of perovskite systems, induced by structural modifications, inspired a focus on multivalent ion doping—chalcogenides and pnictogenides such as $S^{2-}$, $Se^{2-}$ and $N^{3-}$. With nitrogen being overly electronegative, compromises can thus be $S^{2-}$ and $Se^{2-}$. Synergistically, the ease of photoelectron transport[41] and wide absorption spectra in lead chalcogenides is evident by the small bandgaps of lead(II) sulfide (PbS, 0.37 eV) and lead(II) selenide (PbSe, 0.28 eV) that are used as semiconductors.[42-45] Indeed, the difference in electronegativity ($\Delta_\chi$) between Pb and Se is even slightly smaller than that between Pb and I, ($\Delta_\chi$ for Pb—Se=0.68, $\Delta_\chi$ for Pb—I=0.79, on the Pauling Scale). As such, doping with PbSe would minimize any negative impact on the desired covalent nature of the inorganic framework in hybrid perovskite, while allowing for good charge transport.

The proposed crystal structure of 10% w/w PbSe doped $CH_3NH_3PbI_3$ takes into consideration that the periodically located $Se^{2-}$ forms hydrogen-bond like interaction with $CH_3NH_3^+$ in proximity, as illustrated in FIG. 1, confirming that the origin of moisture stability falls on the attracted $CH_3NH_3^+$ groups through strong electrostatic interaction with $Se^{2-}$. Moreover, the addition of $Se^{2-}$ in the perovskite layer mitigates the chemical interaction between iodide and a silver counter electrode.

Figure 9:
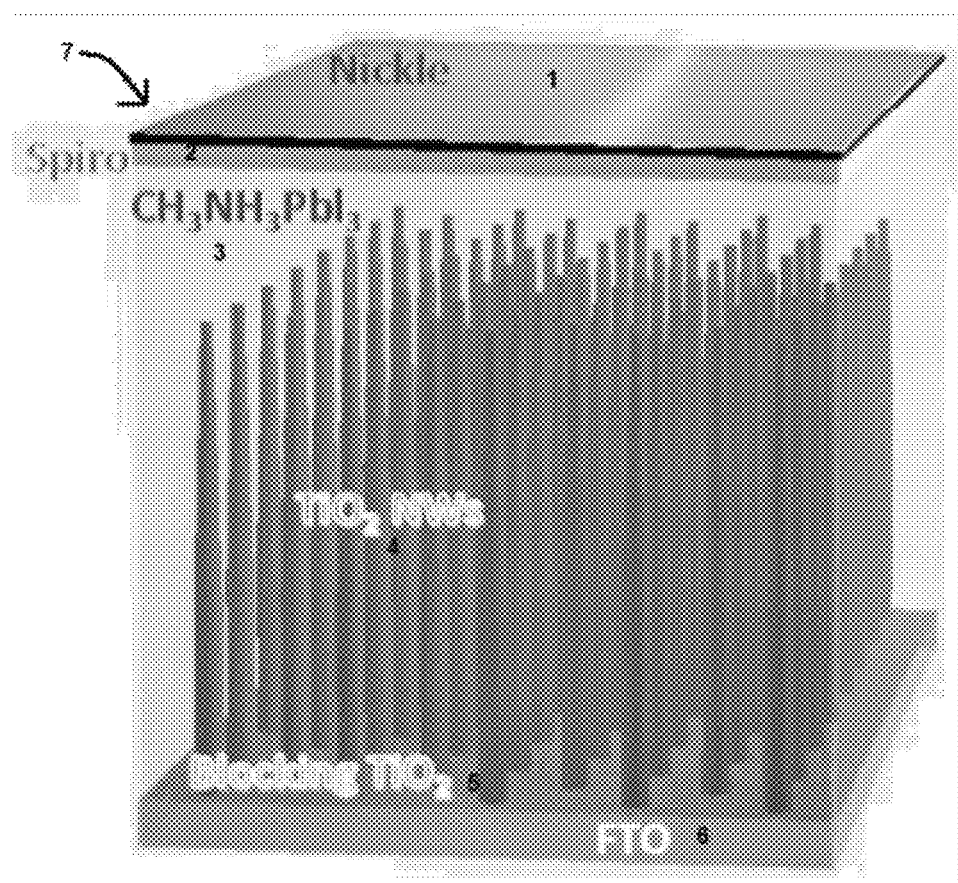
FIG. 9 shows a schematic diagram of a perovskite solar cell with listed components being preferred materials: a fluorinated tin oxide (FTO) anode covered with an electron blocking $TiO_2$ thin film, rutile $TiO_2$ nanowires, spin-coated $CH_3NH_3PbI_3$ layer, or spin-coated $CH_3NH_3Pb(SCN)_2I$ layer and sprio-MeTAD layer, followed by a sputtered nickel cathode.
Figure 10:
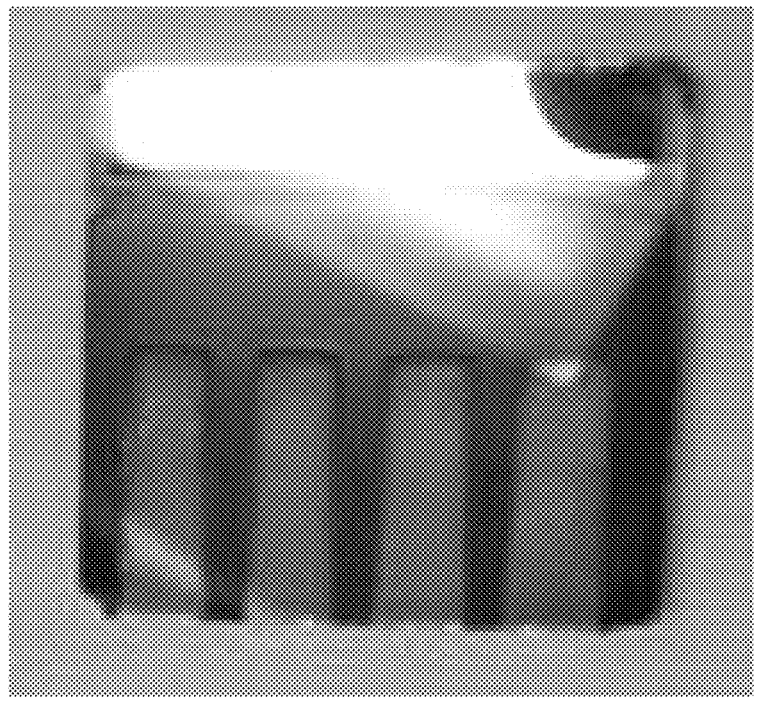
FIG. 10 shows the edges of silver electrodes which have reacted with iodides.

Doped perovskite absorbers can be used in a solar cell as a light-harvesting material, as illustrated in FIG. 9. The solar cell preferably includes a first conductive layer, 6; an optional electron blocking layer, 5, on the first conductive layer, a semiconductor layer, 4, on the optional electron blocking layer; a light-harvesting material, 3, on the semiconductor layer; a hole-transporting material, 2, on the light-harvesting layer; and a second conductive layer, 1, on the hole-transporting material.

Preferably, the first conductive layer is transparent, so that light may penetrate one side of the device and reach the light-harvesting material. Optionally, the first conductive layer may be on a substrate. Examples of substrates include glass, quartz and transparent polymeric materials, such as polycarbonate. Examples of transparent conductive layers include indium-tin oxide, fluorinated tin oxide, and aluminum-zinc oxide. Graphene may also be used as the first conductive layer. The first conductive layer may also be formed as a composite material and/or formed as multiple layers. For example, a planar substrate of glass may be coated with a layer of fluorinated tin oxide, and fine particles of fluorinated tin oxide applied to the surface and sintered together to provide the substrate and first conductive layer.

In an alternative configuration, such as that described in Patent Application Publication, Pub. No. US 2011/0220192, the first conductive layer, with the semiconductor layer and light harvesting material, are on the support, but spaced away from the electrode and second conducting layer, and not in direct electrical contact therewith. In operation of this alternative configuration, light does not need to travel through the first conductive layer, so a non-transparent conductive layer may be used, for example a metal such as nickel, gold, silver or platinum, or a conductive oxide, such as electrically conductive titanium suboxides.

The optional blocking layer, which serves to bind defective sites and suppress back electron transfer, and may have a different composition than the semiconductor layer, and is preferably a transparent insulating material, for example titanium dioxide ($TiO_2$), magnesium oxide (MgO), aluminum oxide ($Al_2O_3$), zirconium oxide ($ZrO_2$), boron nitride (BN), silicon oxide ($SiO_2$), diamond (C), barium titanate ($BaTiO_3$), and mixtures thereof. The blocking layer may also be formed of a transparent semiconductor material and preferably is an n-type semiconductor, for example titanium dioxide ($TiO_2$), zinc oxide (ZnO), zirconium oxide ($ZrO_2$), tungsten oxide ($WO_3$), molybdenum oxide ($MoO_3$), lead oxide (PbO), and mixtures thereof, or mixtures thereof with a transparent insulating material. It is important that the blocking layer be both conformal and compact.

The optional blocking layer preferably has a thickness of at most 20 nm, or may be present in an amount of at most 100 atomic layers. It may also be present as islands on the surface of the semiconductor layer, in which case the thickness may be expressed as an average thickness across the semiconductor layer, for example as less than one atomic layer.

The semiconductor layer, which is n-doped or n-type, may be a transparent semiconductor, such as titanium dioxide ($TiO_2$), zinc oxide (ZnO), zirconium oxide ($ZrO_2$), tungsten oxide ($WO_3$), molybdenum oxide ($MoO_3$), lead oxide (PbO) or mixtures thereof. Preferably, the semiconductor layer has a thickness of at most 100 nm, for example 1 to 100 nm, including 5, 10, 15, 20, 25, 30, 35, 40, 45, 50, 55, 60, 65, 70, 75, 80, 85, 90 and 95 nm. If the semiconductor layer is not intrinsically formed as an n-type semiconductor, such as is the case with $TiO_2$, is may be chemically n-doped.

The semiconductor layer may be formed by physical vapor deposition, such as evaporation or sputtering, or by chemical deposition, such as atomic layer deposition, or by forming a thin layer of a precursor which is then decomposed to form the semiconductor layer. Electrochemical deposition or deposition from solution, may also be used in the case of conductive polymers. The thickness may be controlled by the amount of semiconductor initially deposited, or by removing deposited semiconductor by etching, such as chemical etching. The semiconductor layer may also be formed by applying a dispersion of fine particles of the semiconductor dispersed into a fluid, for example particles have an average diameter of 5 to 100 nm, including 10, 20, 30, 40, 50, 60, 70, 80 or 90 nm, dispersed in water, or an organic solvent for example alcohols such as methanol or ethanol, or mixtures thereof. Sintering may be desirable to remove the solvent and/or improve the contact between the semiconductor layer and the first conductive layer, or to improve the crystallinity of the semiconductor layer. It is important that the semiconductor layer both conformal and compact. Ideally, the contact between the first conductive layer and the semiconductor layer should be an ohmic contact.

Atomic layer deposition may be carried out by chemical reaction of two compounds which react to form the semiconductor layer. The structure onto which the semiconductor layer is to be deposited is exposed to vapors of the first of the two chemicals, and then exposed to the vapors or gasses of the second of the two chemicals. If necessary, the exposure and/or reaction may be carried out at elevated temperatures. In some instances, byproducts of the reaction may need to be removed before repeating the process, by washing, evacuation, or by the passage of an inert gas over the structure. The process may be repeated until the desired thickness of the semiconductor layer is formed. For example, in the case of the transparent oxide semiconductors, which are typically compounds of a metal and oxygen, the first chemical may be a halide, such as a chloride, bromide or iodide, an oxychloride, oxybromide or oxyiodide, organometallic compounds, alkoxides of the metal and other ceramic precursor compounds (such as titanium isopropoxide), as well as mixtures thereof. The second chemical may be water ($H_2O$), oxygen ($O_2$ and/or $O_3$) or a gaseous oxidizing agent, for example $N_2O$, as well as mixtures thereof. Inert gasses, such as helium, argon or nitrogen may be used to dilute the gasses during the process.

In a preferred alternative embodiment, the semiconductor layer is composed of $TiO_2$ nanowires. The nanowires may be prepared by solvothermal method with controllable length-to-diameter ratio and are well separated.[78] Preferably, the length of the TiO$_2$ nanowires is 400-1100 nm, more preferably 600-1000 nm, including 700, 800 and 900 nm.

The light-harvesting material is preferably a perovskite absorber. A "perovskite absorber" is a compound of formula ABX$_3$, where A is a metal atom such as lead or tin, B is a counter ion (typically an alkyl ammonium compound), and X is a halide (F, Cl, Br, or I) or pseudohalide (such as SCN), which forms crystals of the perovskite structure. Examples include CH$_3$NH$_3$PbX$_3$ (3-dimensional perovskite) and H$_2$NCHNH$_2$PbX$_3$ (3-dimensional perovskite) and CH$_3$NH$_3$Pb(SCN)$_2$I (Ruddlesden-Popper type). Examples of structure which are perovskite structures included 3-dimensional perovskite, Ruddlesden-Popper type and Dion-Jacobson type. In some cases, the perovskite absorber is doped, which may result in additional atoms located in interstitial sites and/or the formation of vacancies. Examples of a perovskite absorber that is doped included CH$_3$NH$_3$PbI3:10% PbSe, which is CH$_3$NH$_3$PbI$_3$ doped with 10% PbSe, and therefore the stoichiometry may deviate from the ABX$_3$ formula.

Preferably, the light-harvesting material is applied by spin-coating so that it fills spaces on and in the semiconductor layer. Preferably, the perovskite absorber is doped with PbSe. Preferably the perovskite material is doped with 5 to 20% PbSe, most preferably with 9-11% PbSe.

The hole-transporting material may be a solid p-type semiconductor, for example CuI, CuSCN, CuAlO$_2$, NiO, and mixtures thereof, as well as p-doped conductive polymers. Conductive polymers include poly(acetylene)s, poly(pyrrole)s, poly(thiophene)s, polyanilines, polythiophenes, poly(p-phenylene sulfide), poly(para-phenylene vinylene)s (PPV) and PPV derivatives, poly(3-alkylthiophenes), polyindole, polypyrene, polycarbazole, polyazulene, polyazepine, poly(fluorene)s, and polynaphthalene. Other examples include polyaniline, polyaniline derivatives, polythiophene, polythiophene derivatives, polypyrrole, polypyrrole derivatives, polythianaphthene, polythianaphthane derivatives, polyparaphenylene, polyparaphenylene derivatives, polyacetylene, polyacetylene derivatives, polydiacetylene, polydiacetylene derivatives, polyparaphenylenevinylene, polyparaphenylenevinylene derivatives, polynaphthalene, and polynaphthalene derivatives, polyisothianaphthene (PITN), polyheteroarylenvinylene (ParV), in which the heteroarylene group can be for example thiophene, furan or pyrrol, polyphenylene-sulphide (PPS), polyperinaphthalene (PPN), and polyphthalocyanine (PPhc), and their derivatives, copolymers thereof and mixtures thereof. As used herein, the term derivatives means the polymer is made from monomers substituted with side chains or groups. P-doping of the solid semiconductor and the conductive polymers may be carried out chemically, if necessary, for example by treatment with an oxidizing agent, such as oxygen, fluorine or iodine, or by electrochemical oxidation. A preferred hole-transporting material is spiro-MeOTAD (2,2'7,7'-tetrakis(N,N-di-p-methoxyphenyl amine)-9,9'-spirobifluorene).

A second conductive layer is in contact with the hole-transporting material, and is preferably formed of a highly conductive and chemically unreactive material, for example gold, platinum, or metallic alloys. Preferably, the second conductive layer is nickel or a nickel alloy. The second conductive layer may be present on a third conductive layer, which may be formed of any conductive material. The second conductive layer serve to transport electrons back to the hole-transporting material, thus completing the electrical circuit. The second conductive layer is preferably on a support, which may be formed of any solid material, such as plastic, glass or metal. Preferably, the second conductive layer is formed by evaporation or sputtering.

EXAMPLES

Chemicals and Materials Synthesis

Methylamine solution (CH$_3$NH$_2$, 40 wt. % in H$_2$O) and γ-Butyrolactone (GBL, ≥99%) were purchased from Aldrich. Hydriodic acid (HI, 57% w/w aq. soln.), lead(II) iodide (PbI$_2$, 99.9985% metals basis) and N,N-Dimethylformamide (DMF, anhydrous) were purchased from Alfa Aesar. Ethyl ether (anhydrous), and hydrochloric acid (HCl, 37.0%) were purchased from Fisher Chemical. Lead acetate (Pb(C$_2$H$_3$O$_2$)$_2$.3H$_2$O) was purchased from Mallinckrodt and sodium sulfide Na$_2$S.9H$_2$O was purchased from Aldrich. All chemicals were used without further purification.

Perovskite films were prepared through a combination of PbI, methylammonium iodide and PbSe or PbS. PbI was purchased through Alfa Aesar without additional processing. Methylammonium lead iodide was synthesized using a 1:1.5 molar ratio of HI (Sigma) and methylamine (Sigma Aldrich). This was mixed, and washed with ether to produce a white crystalline solid. PbSe was synthesized using lead acetate (Alfa Aesar) and selenium oxide. Selenium oxide was dissolved in water and adjusted to a pH of 1. Lead acetate was then added and a white precipitate formed, which was washed thoroughly with deionized water. PbS was synthesized through the addition of Na$_2$S (Sigma Aldrich) to lead acetate in aqueous environment in a 1:1 molar ratio. The resulting black precipitate was washed 5 times with deionized water and allowed to dry at 100° C. Solutions were made using a 9:1 ratio of PbI$_2$:PbS without changing the concentration of methyl ammonium iodide. Care was taken to reduce oxidation of PbS and PbSe powders after preparation.

CH$_3$NH$_3$I was synthesized according to methods reported in literature[12] with slight modifications. In detail, HI was slowly introduced to equimolar CH$_3$NH$_2$ in a 200 mL round bottom flask immersed in an ice bath, with the solution being stirred continuously. The solution was allowed to react for 2 hours under stirring, then rotary evaporated at 60° C. until all solvent was removed. As obtained yellow solid was washed with ethyl ether six times, followed by vacuum filtration. Finally, the solid was dried at 120° C. in an oven overnight to give pure CH$_3$NH$_3$I product, exhibiting a white color. PbSe was synthesized by first adjusting an aqueous solution of SeO$_2$ to a pH of 2 using HCl, which was then mixed with Pb(C$_2$H$_3$O$_2$)$_2$.3H$_2$O in a 1:1 molar ratio. The solution was stirred for 12 hours at 80° C. The resulting white-pink solid was washed 5 times with excess deionized water and dried in an oven at 120° C. overnight.[46] The obtained powder was characterized using EDX measurements to confirm the purity of PbSe. Similarly, PbS was synthesized by adding equimolar amounts of Pb(C$_2$H$_3$O$_2$)$_2$.3H$_2$O and Na$_2$S.9H$_2$O to deionized water and allowing to stir for a 1 hour. The resulting black precipitate was washed thoroughly with deionized water and characterized with EDX to confirm purity.

Solution Synthesis

In the case of 10 w/w % of PbSe doping, it is defined as 10 w/w % of PbSe in the initial total mass of PbSe and PbI$_2$. Explicitly, 0.04 g of PbSe was dissolved in 0.7 ml of γ-butyrolactone with 0.360 g PbI$_2$ and 0.149 g CH$_3$NH$_3$I, resulting in a 9:1 weight ratio of PbI$_2$ to PbSe. The resulting mixture was stirred at 80° C. for 15 hours to yield a dark red solution. The doping level of PbS is similarly defined.

Accelerated Moisture Stability Experiment Setup

The accelerated moisture stability tests were carried out in a modified, glass-enclosed two-chamber system. The internal glass chamber was suspended in 40° C. deionized water inside of a larger glass vessel and held the tested samples, keeping the samples from direct contact with the liquid water. The external chamber was filled partially with deionized water, covered and heated to 40° C. The chamber was exposed to ambient light. This set up allowed the samples in the internal chamber to be exposed to water vapor generated in the surrounding water bath without direct contact to the water. The humidity was tested using a portable humidity tester and confirmed at 100% once the temperature reached 40° C.

Figure 2A:
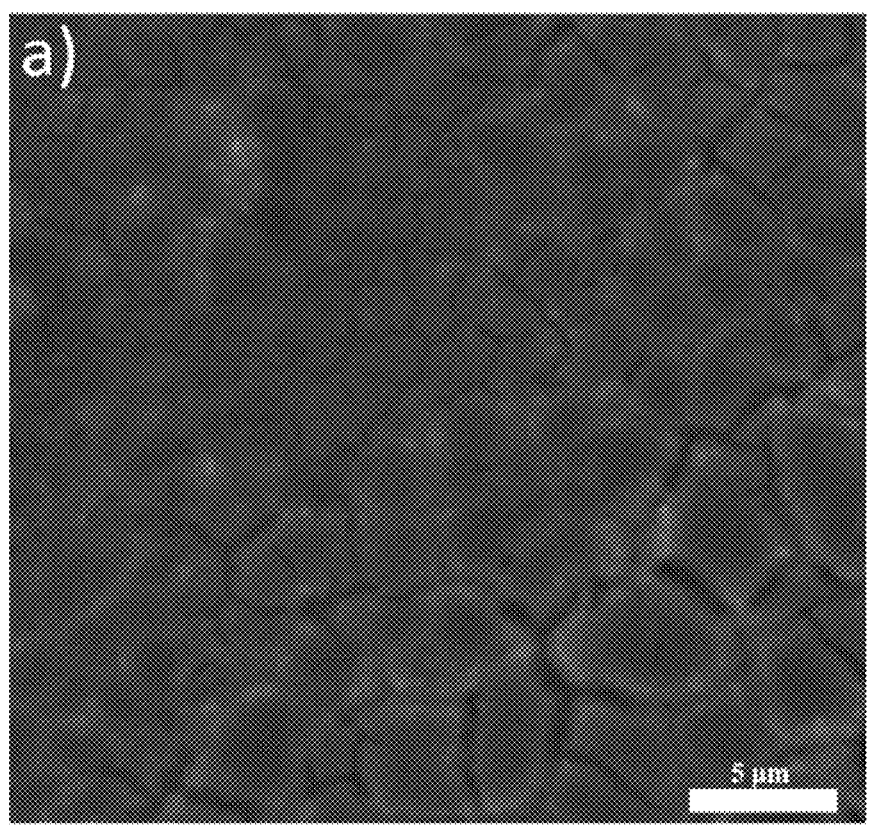
FIG. 2A shows a SEM image of surface morphology of 10% w/w PbSe doped $CH_3NH_3PbI_3$ thin film.
Figure 2B:
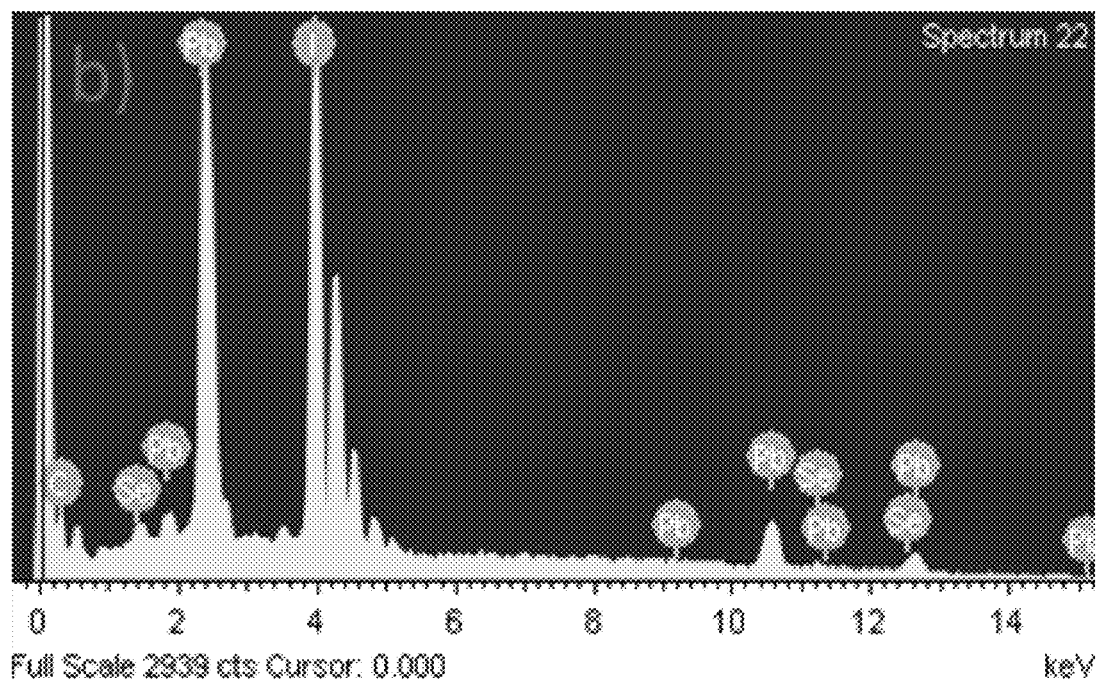
FIG. 2B shows an energy dispersive X-ray analysis of 10% w/w PbSe doped $CH_3NH_3PbI_3$ thin film.

Both pristine $CH_3NH_3PbI_3$ and PbSe-doped $CH_3NH_3PbI_3$ films were deposited on $TiO_2$-coated FTO glass substrates by spin coating at speed of 2000 rpm, followed by annealing at 120° C. for 60 minutes. It was previously demonstrated that single-step spin-coating of pure $CH_3NH_3PbI_3$ precursor solution results in thin films with low surface coverages, non-uniform thicknesses and varying crystal structures riddled with pin holes,[4,15,47,48] which subsequently plagues charge transport in solar cells by means of short circuiting the material and causing decreased range electron transfers. Surprisingly, single-step deposition of PbSe-doped $CH_3NH_3PbI_3$ precursor solution leads to films with high surface coverage and large-size grains, without the need for anti-solvent use, as shown in FIG. 2A. However, cracks between large grains are observed, which may be due to the inherent nature of perovskites, as the films form from nucleation points, creating large "grains" and inherent grain boundaries. In order to confirm the existence of Se in 10% w/w PbSe doped sample, we set out to perform energy-dispersive X-ray analysis (EDX) on the fabricated thin film. FIG. 2B shows the EDX spectrum of spin-coated 10% w/w PbSe doped $CH_3NH_3PbI_3$ thin film. Clearly, the spectrum confirms the findings of Se, through the peaks at around 1.4 keV, 11.2 keV and 12.5 keV energies. Additionally, the spectrum also indicates the persistence of Pb and I, which are the main components of inorganic framework of perovskite $CH_3NH_3PbI_3$. Characteristically, Pb was identified through peaks at around 1.8 keV, 2.4 keV, 10.6 keV and 12.6 keV. The high intensities of Pb and I signals as illustrated in the spectrum account for the natures of Pb and I being electron-rich atoms that have strong interactions with X-rays. Qualitatively, Table 1, below, summarizes the elemental analysis by EDX confirming the desired amount of PbSe present in the prepared film compared to theoretically calculated percentages. Nitrogen was removed from the calculations due to overlapping carbon and nitrogen peaks, artificially increasing the percentage of both carbon and nitrogen. This further allowed for a more accurate percentage of low concentration atoms to be calculated. In Table 1 the average was taken based on the three separate measurements. Each measurement was taken at a different point on the thin film surface.

TABLE 1

Summary of EDX measurements for 10% w/w PbSe doped $CH_3NH_3PbI_3$.

| Element | Weight % | Weight % | Weight % | Av. Weight % | Theoretical for 10 w % |
|---|---|---|---|---|---|
| C | 5.29 | 5.42 | 5.40 | 5.37 | 2.1% |
| Se | 1.03 | .93 | .81 | .92 | 1.3% |
| I | 59.59 | 60.16 | 62.30 | 60.69 | 61.83% |
| Pb | 34.10 | 33.50 | 31.49 | 33.03 | 34.8% |

Figure 2C:
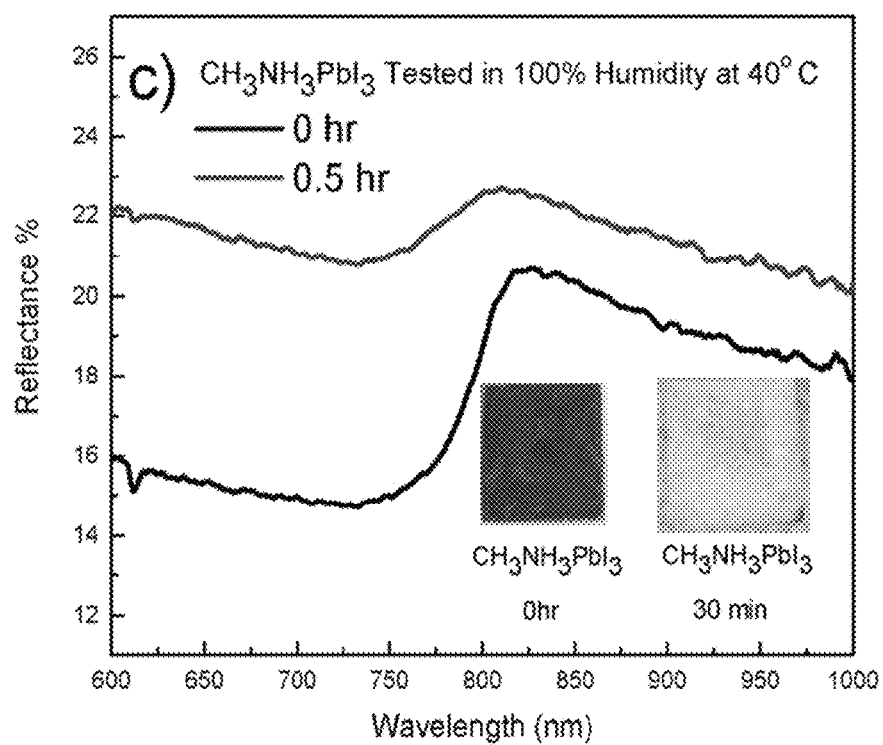
FIG. 2C shows evolution of time-dependent reflectance spectra of pristine $CH_3NH_3PbI_3$ under 100% humidity at 40° C. under ambient illumination conditions.
Figure 2D:
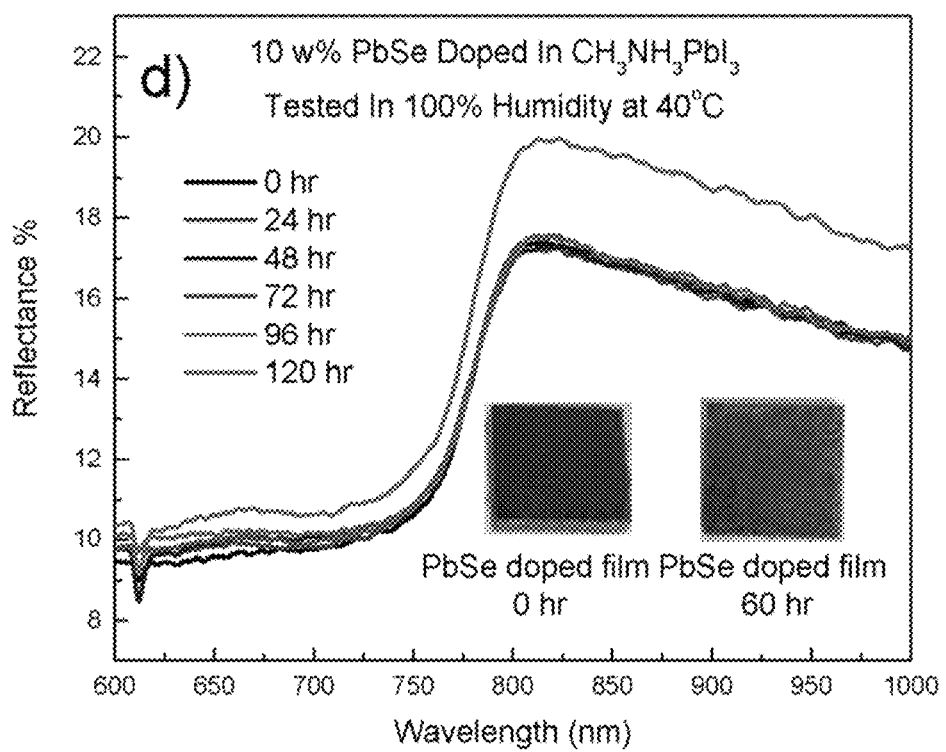
FIG. 2D shows evolution of time-dependent reflectance spectra of 10% w/w PbSe doped $CH_3NH_3PbI_3$ thin films under 100% humidity at 40° C. under ambient illumination conditions.
Figure 4:
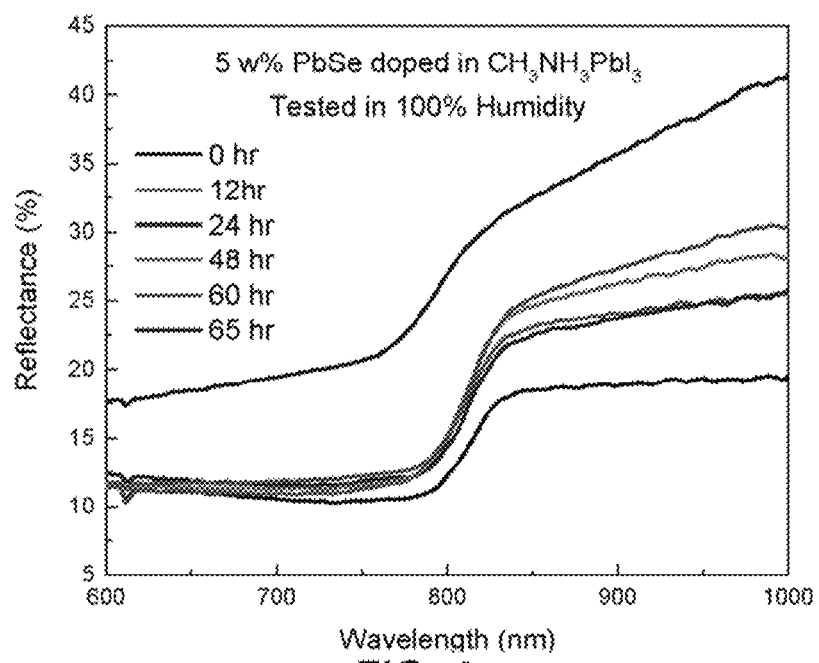
FIG. 4 is a stability graph showing water stability based on reflectance percent of 5% w/w doped $CH_3NH_3PbI_3$.
Figure 5:
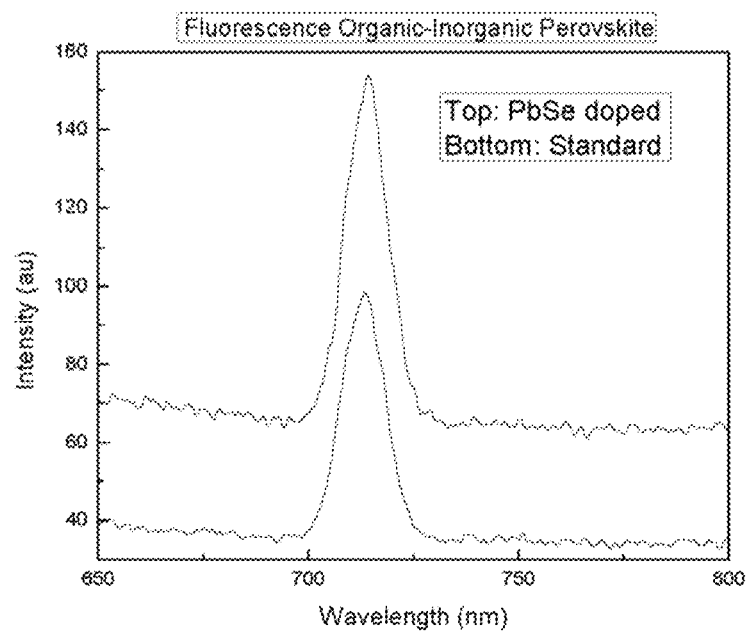
FIG. 5 shows fluorescence intensity of PbSe doped perovskite versus undoped perovskite.
Figure 11A:
FIG. 11A shows a photograph of tested $CH_3NH_3PbI_3$ film at 0 minutes of aging time.
Figure 11B:
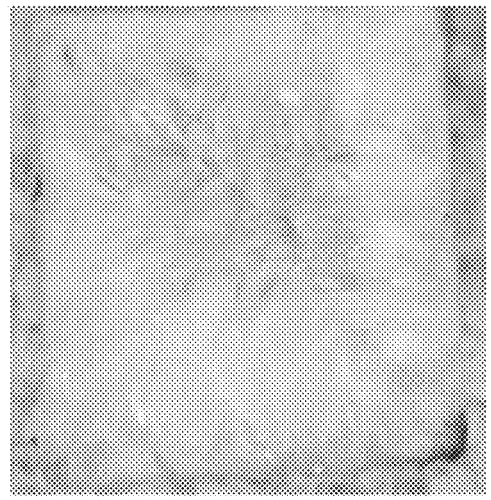
FIG. 11B shows a photograph of tested $CH_3NH_3PbI_3$ film at 30 minutes of aging time.
Figure 12A:
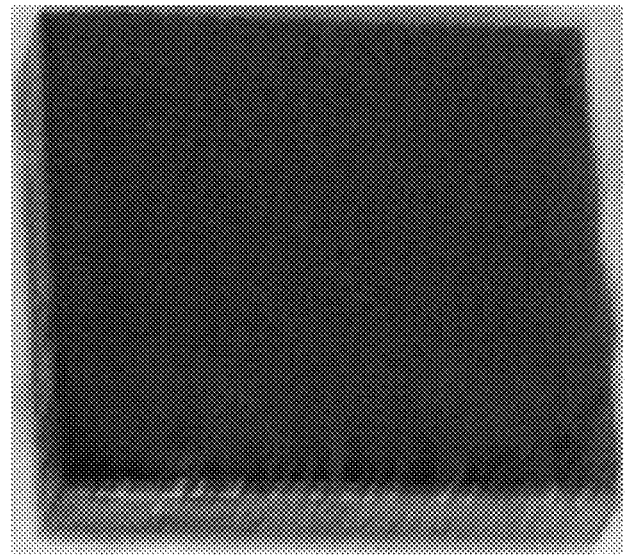
FIG. 12A shows a photograph of tested 10% w/w PbSe doped $CH_3NH_3PbI_3$ film at 0 minutes of aging time.
Figure 12B:
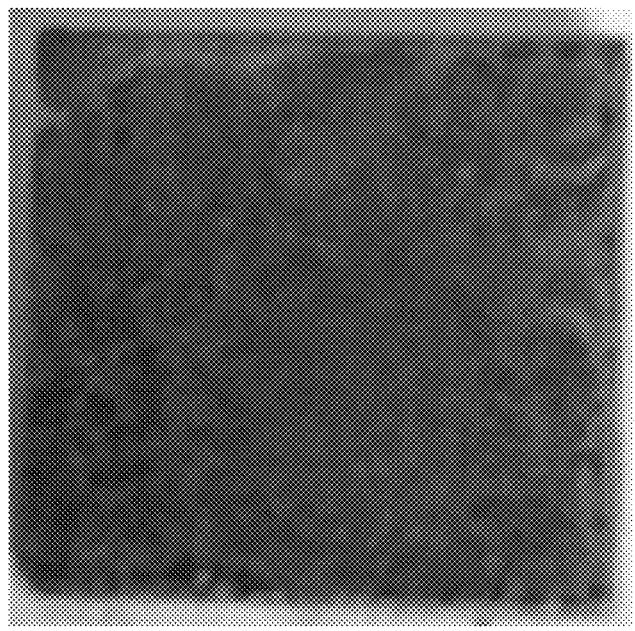
FIG. 12B shows a photograph of tested 10% w/w PbSe doped $CH_3NH_3PbI_3$ film at 60 minutes of aging time.

The evaluations of the moisture stabilities of pristine $CH_3NH_3PbI_3$ and 10% w/w PbSe-doped $CH_3NH_3PbI_3$ films were conducted by time-dependent reflectance measurements, at an accelerated manner, with the details of accelerated moisture-exposure experiment setup given in Experimental Details section. The reflectance spectra of both films show the change of optical reflectance spectra as a function of exposure time in 100% humidity under ambient illumination. FIG. 2C shows the evolution of reflectance of pristine $CH_3NH_3PbI_3$ thin film, with inset pictures being the photographs of tested film at 0 minute (left) and 30 minutes (right) of aging time. At initial time of moisture exposure (black plot), $CH_3NH_3PbI_3$ film displays a reflectance profile where the percentage of light reflected is low (<~16%) between 600 and 775 nm. Reflectance then elevates drastically between 775 nm and 825 nm which notes the onset of material reflectance. Even only after 30 minutes of moisture exposure (red plot), the aged $CH_3NH_3PbI_3$ film already shows an apparent blue shift of reflectance onset, along with the total upshift in amount of light reflected. The $CH_3NH_3PbI_3$ experienced significant degradation after aging in ~100% moisture environment for only 30 minutes based on our test conditions. In phenomenal contrast, FIG. 2D shows the evolution of reflectance of 10% w/w PbSe doped $CH_3NH_3PbI_3$ film, with insets also being photographs of tested films at corresponding aging times (0 hour, left; 60 hours, right). FIG. 11A shows a photograph of tested $CH_3NH_3PbI_3$ film at 0 minutes of aging time. FIG. 11B shows a photograph of tested $CH_3NH_3PbI_3$ film at 30 minutes of aging time. The closely overlapped time-dependent spectra from 0 hours up to even 96 hours of 10% w/w PbSe doped $CH_3NH_3PbI_3$ film, demonstrates enhanced moisture stability. Defining "stability" as the stability of the reflectance spectra over exposure time in 100% humidity under ambient illumination, the 10% w/w PbSe doped $CH_3NH_3PbI_3$ film exhibits over two-hundred-fold stability compared to the pure $CH_3NH_3PbI_3$. FIG. 2D shows that the final degradation of 10% w/w PbSe-doped $CH_3NH_3PbI_3$ occurred after 120 hours, as shown by the increase in reflectance at 800 nm from 15% to 20%. FIG. 12A shows a photograph of tested 10% w/w PbSe doped CH3NH3PbI3 film at 0 minutes of aging time. FIG. 12B shows a photograph of tested 10% w/w PbSe doped $CH_3NH_3PbI_3$ film at 60 minutes of aging time. To validate the trend of doping effects on the evolution of reflectance spectra, we also performed reflectance tests on 5% w/w PbSe-doped $CH_3NH_3PbI_3$ films, as shown in FIG. 4. Results confirm that as the doping percentage decreased, so did the chemical stability of the film. Utilizing half of the dopant concentration, the stability of the resultant film exhibited a little more than half of the stability of the 10% w/w film, lasting a remarkable 65 hours in humid air. This confirms that the stability is dependent on the concentration of dopant used and follows a steady trend relative to concentration.

Figure 2E:
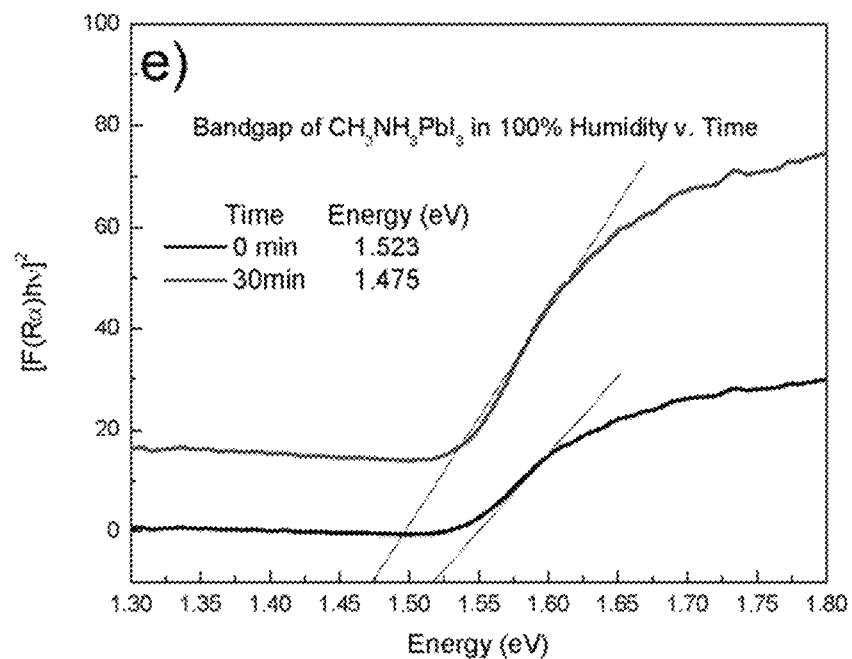
FIG. 2E shows Kubelka-Munch plots of pristine $CH_3NH_3PbI_3$ thin films.
Figure 2F:
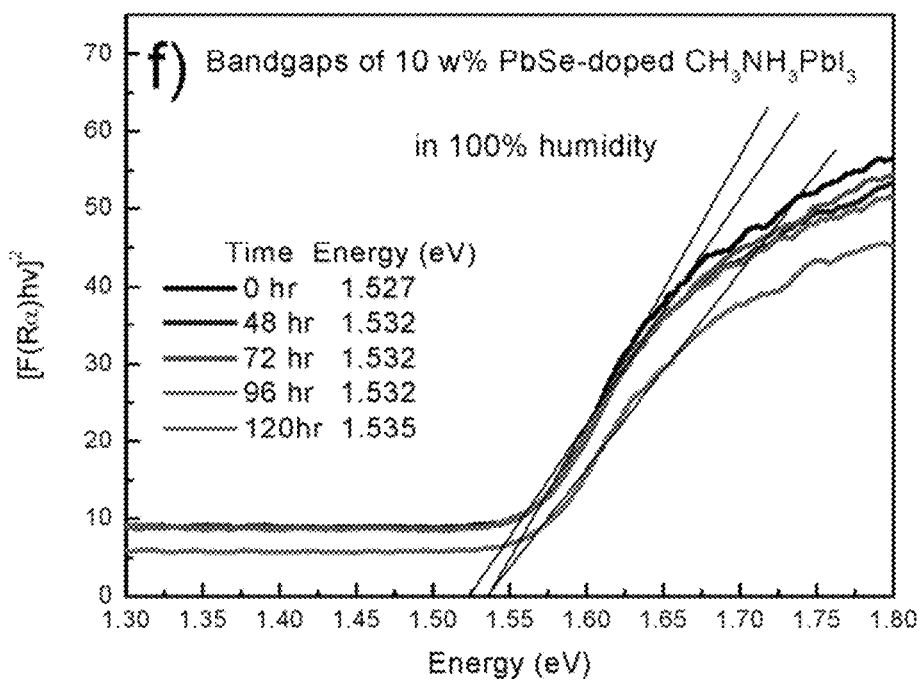
FIG. 2F shows Kubelka-Munch plots of 10% w/w PbSe doped $CH_3NH_3PbI_3$ thin films.

FIG. 2F presents the band gap for 10% w/w PbSe-doped $CH_3NH_3PbI_3$, which exhibited an increase after 48 hours from 1.527 eV to 1.532 eV, most likely due to the formation of a stable hydrated crystal, finally degrading at 1.535 eV. Likewise, FIG. 2E shows the corresponding bandgap for pristine $CH_3NH_3PbI_3$, with corresponding band gap of 1.535 eV and a degraded bandgap at 1.475 eV. Obviously, the band gap of PbSe-doped $CH_3NH_3PbI_3$ changed little and was shown to be comparable with that of reported pure $CH_3NH_3PbI_3$ perovskite film, which exhibits a band gap of 1.53-1.54 eV. This remarkably enhanced stability in moisture can be attributed to the structural integrity through electrostatic interaction between $Se^{2-}$ and the adjacent positively charged methylammonium cations. The electrostatic interaction reduces the detrimental effect of atmospheric water by washing out the cationic organic moieties. Previous studies have shown evidence of hydrogen-bonding-like electrostatic interaction between inorganic framework and methylammonium cations.[49-51] If water does penetrate the lattice, the increased covalent nature of the PbSe bonding stabilizes the lattice, and allows for retained rigidity and durability of the crystal lattice. From a fundamental material synthesis view, increasing electrostatic interactions at a balanced level will further allow chemical stability and integrity in perovskite materials.

Figure 2G:
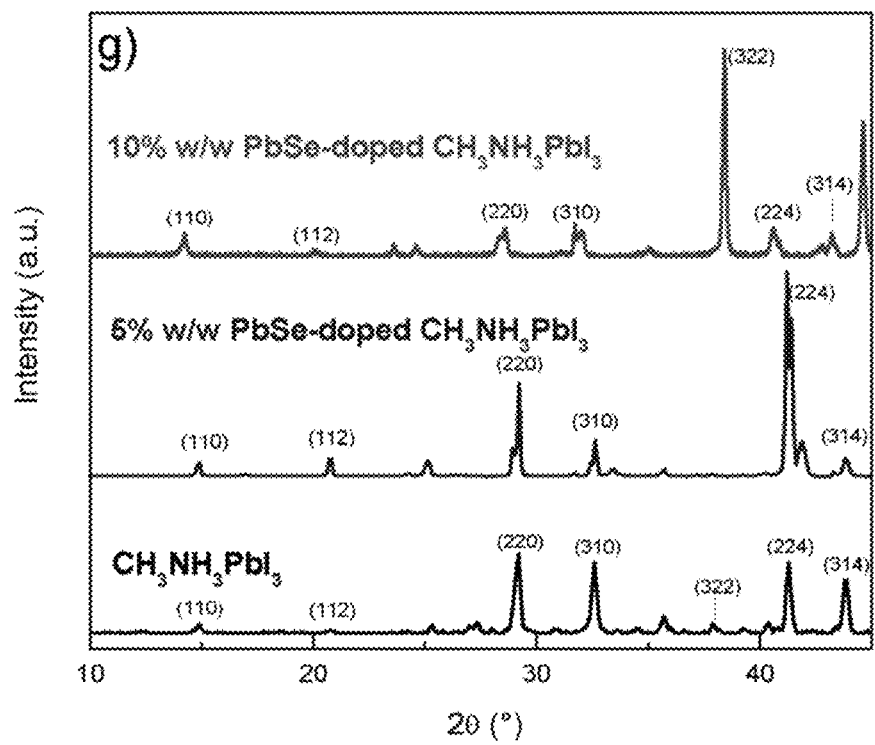
FIG. 2G shows powder X-ray diffraction spectra of pristine $CH_3NH_3PbI_3$ (bottom), 5% w/w PbSe doped $CH_3NH_3PbI_3$ (middle) and 10% w/w PbSe doped $CH_3NH_3PbI_3$ (top) samples, with crystallographic planes indicated above corresponding diffraction peaks of each trace to illustrate the shift of diffraction angles.

As presented in previous studies, increasing the cubic nature (P4 mm, Pm3m) of perovskite (peaks at 2θ=14°, 23°, 29°, 32°, 41°) and reducing the orthogonal/tetragonal nature (Pnma, I4/mcm respectively) (peaks at 2θ=28°, 31°, 44°) in hybrid organic-inorganic perovskites imparts an inherent chemical stability to the material.[51,52] This phenomenon has been observed with the introduction of formamidinium and inorganic dopants.[53,54] FIG. 2G reinforces this observation, showing that all of the inherently cubic peaks increase while the orthogonal/tetragonal peaks show an inherent decrease in relative intensity when doped with PbSe. There are no peaks for PbSe, supporting the idea that the $Se^-$ ions are incorporated into the lattice structure, rather than as a separated phase. From a fundamental level, the Jahn-Teller effect predicts that as the covalent nature increases and the size of dopant atoms decreases, the lattice will shift to a more cubic nature with higher linearity in the bond structure. The identifiable peaks exhibit a fundamental property of hybrid organic-inorganic perovskites, that is, by changing the nature and crystalline phase of the perovskite from a tetragonal dominant phase to a cubic dominant phase, a higher overall water resistance can be achieved.

Figure 2H:
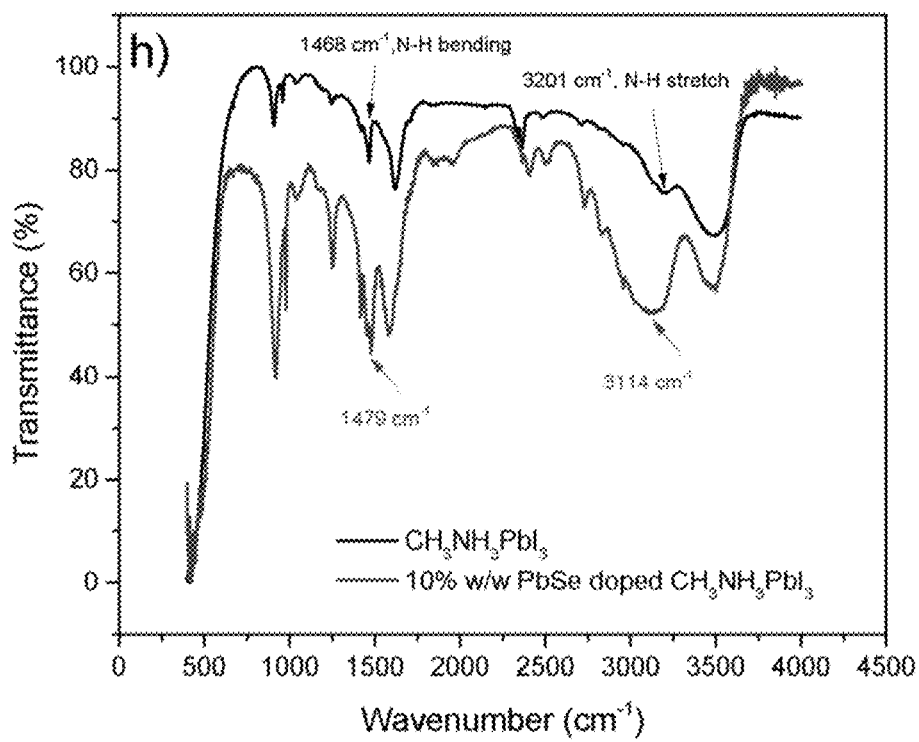
FIG. 2H shows infrared transmittance spectra of $CH_3NH_3PbI_3$ thin film (darker) and 10% w/w PbSe doped $CH_3NH_3PbI_3$ thin film (lighter).

In order to verify the proposed electrostatic attraction between incorporated $Se^{2-}$ and cationic $CH_3NH_3^+$, pristine $CH_3NH_3PbI_3$ and 10% w/w PbSe doped $CH_3NH_3PbI_3$ thin films were further characterized on infrared spectroscopy to illustrate N—H vibrations, by means of frequency changes associated with the affected N—H vibrations. FIG. 2H shows the infrared spectra of $CH_3NH_3PbI_3$ (darker) and 10% w/w PbSe doped $CH_3NH_3PbI_3$ (lighter) thin films, with peak at around 3201 $cm^{-1}$ of $CH_3NH_3PbI_3$ corresponds to N—H stretch.[40,58,59] N—H stretching modes at 3201 $cm^{-1}$ in $CH_3NH_3PbI_3$ films is redshifted to about 3114 $cm^{-1}$ in 10% w/w PbSe doped films due to the electrostatic attraction effects between the $Se^{2-}$ and cationic $CH_3NH_3^+$. This demonstrates that electronegative particles retard stretching modes of atoms when it comes to linearly aligned interactions, such as hydrogen bonding.[60] Also, significant band broadening is witnessed on N—H stretch in 10% w/w PbSe doped $CH_3NH_3PbI_3$, relative to the peak of N—H stretch in pristine $CH_3NH_3PbI_3$. This band broadening suggests the existence of strong electrostatic interaction in material systems.[61] Apart from the redshift of stretching frequency, no obvious change of N—H bending frequency was observed between $CH_3NH_3PbI_3$ and doped $CH_3NH_3PbI_3$ thin-film samples. This is likely due to the two-dimensional bending modes along with the relatively scarce $Se^{2-}$ (~18 mol %) in the doped system, that cannot enable a spatially favored electronic wave function overlap between partially cationic ammonium hydrogen atoms and anionic $Se^{2-}$. Extended X-ray absorption fine structure (EXAFS) spectroscopy was used to verify the intercalation of $Se^{2-}$ into the crystal lattice of $CH_3NH_3PbI_3$, rather than as a separate phase.

Figure 6A:
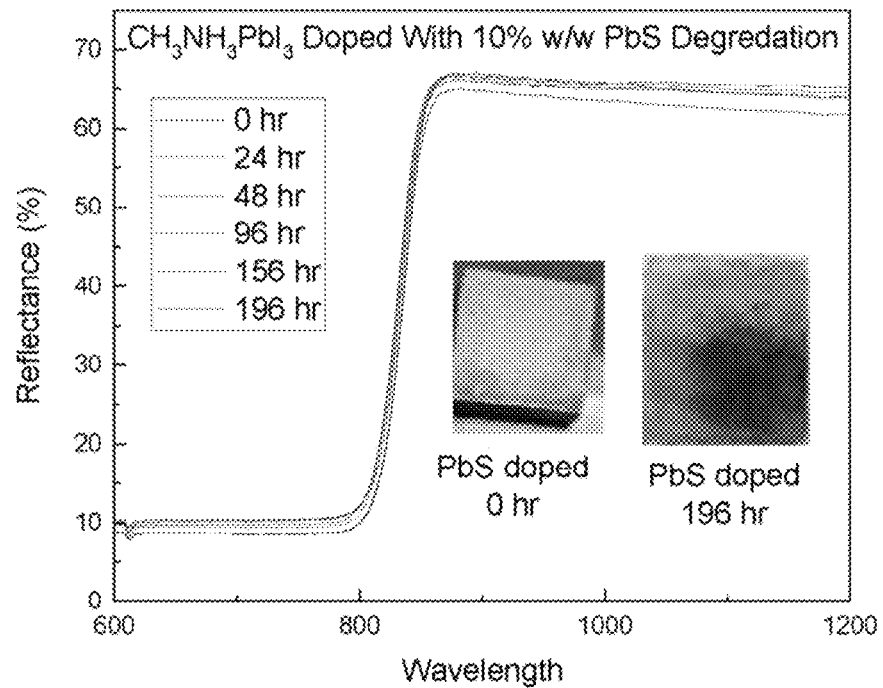
FIG. 6A shows a stability plot of PbS doped $CH_3NH_3PbI_3$ in 100% humidity under ambient light, with photograph insets showing the change in the PbS doped material.
Figure 6B:
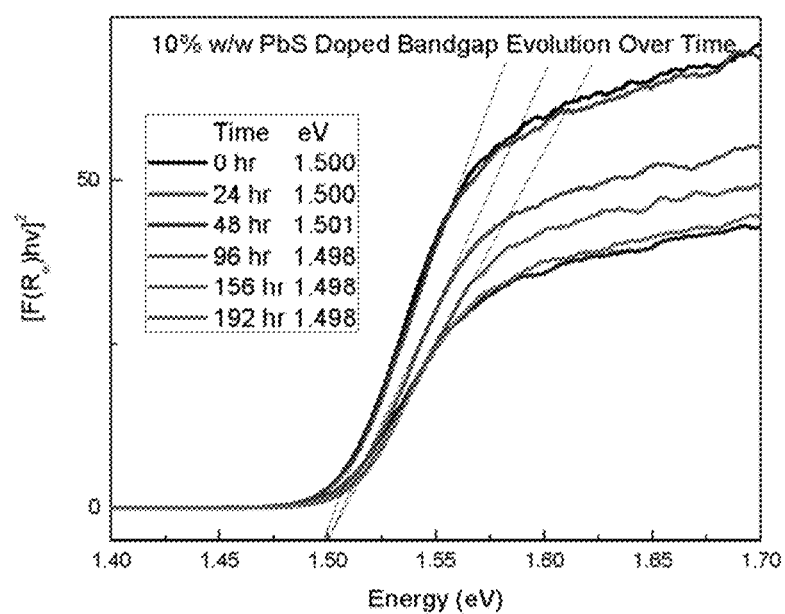
FIG. 6B is a graph of bandgap evolution over time of 10% w/w doped $CH_3NH_3PbI_3$.
Figure 7:
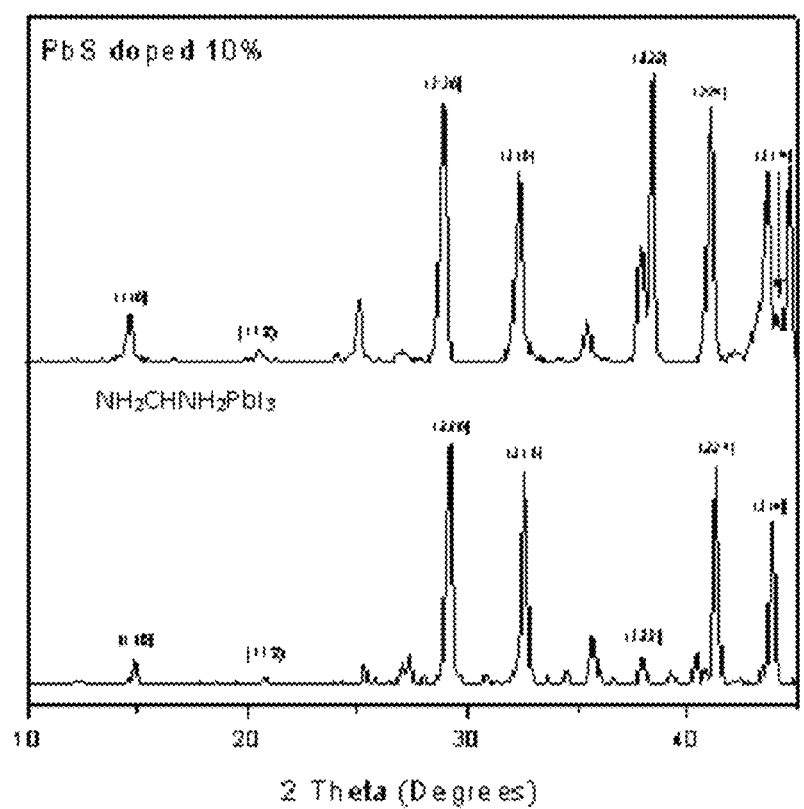
FIG. 7 shows XRD spectra of 10% w/w PbS doped methyl ammonium lead iodide (top) and formamidinium lead iodide (bottom).
Figure 8:
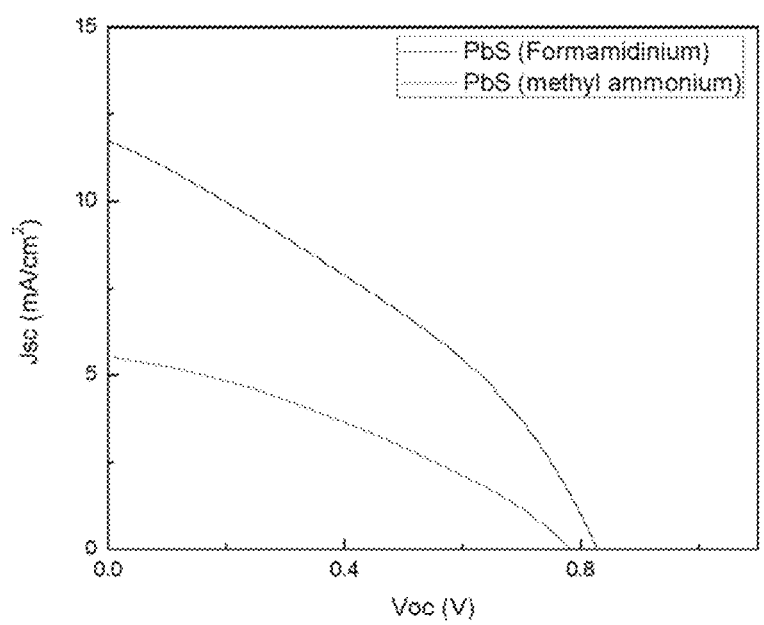
FIG. 8 shows a J-V plot of PbS doped formamidinium lead iodide (darker) and methyl ammonium lead iodide (lighter).

To further solidify the fundamental interactions of chalcogenide doping in organic-inorganic perovskites, bivalent sulfide in the form of PbS, was also tested as an alternative chalcogenide dopant, with S having a greater electronegativity than Se. As shown in FIG. 6A and FIG. 6B, PbS-doped $CH_3NH_3PbI_3$ exhibits an even greater improved stability in humid environments. However, due to its higher ionic nature, and small ionic radius, a lower photovoltaic performance of PbS-doped $CH_3NH_3PbI_3$-based solar cells was observed as shown by the J-V curve in FIG. 8. Although PbS may not be a suitable dopant in this regard, the PbS-doped $CH_3NH_3PbI_3$ film, the results provide support for the fundamental interactions occurring through chalcogenide doping, in regard to stability to moisture. The same trend as PbSe-doped $CH_3NH_3PbI_3$ can be seen in the XRD pattern of PbS doped $CH_3NH_3PbI_3$ (FIG. 7), and this result strengthens the claims that as cubic nature increases, as observed with XRD, tetragonal/orthorhombic nature decreases, and chemical stability of the perovskite material increases. Thus, we show that electronegativity effect is supported by both PbSe and PbS doping.

Figure 3A:
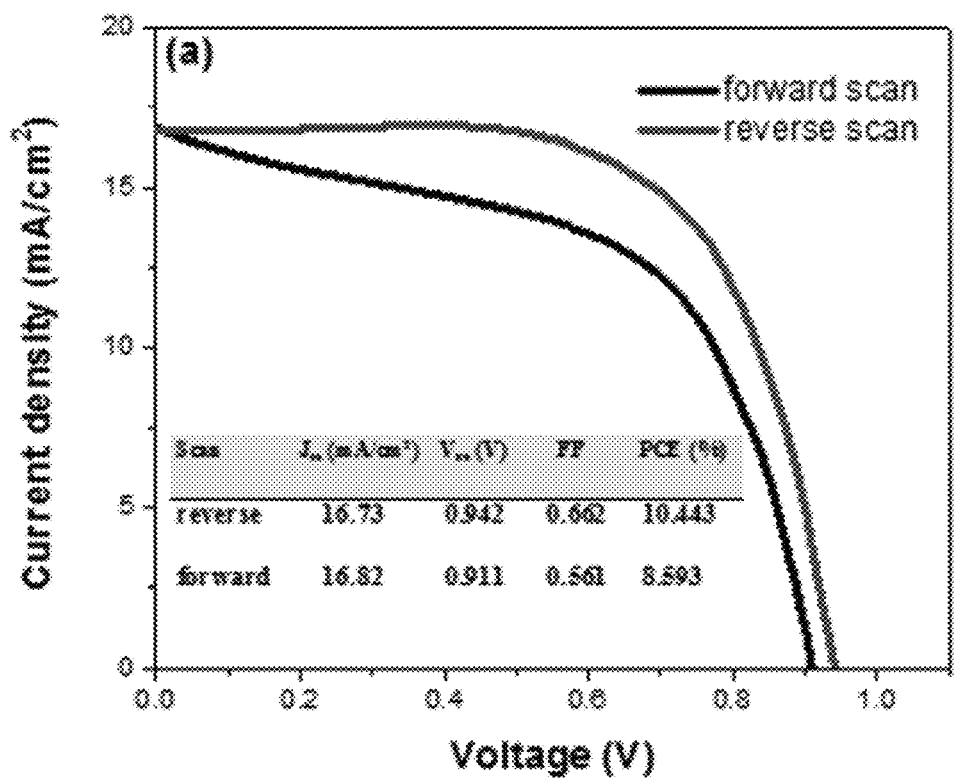
FIG. 3A shows Photocurrent density-voltage (J-V) curves with forward (darker) and reverse (lighter) scans for 10% w/w PbSe doped $CH_3NH_3PbI_3$ champion cell.
Figure 3B:
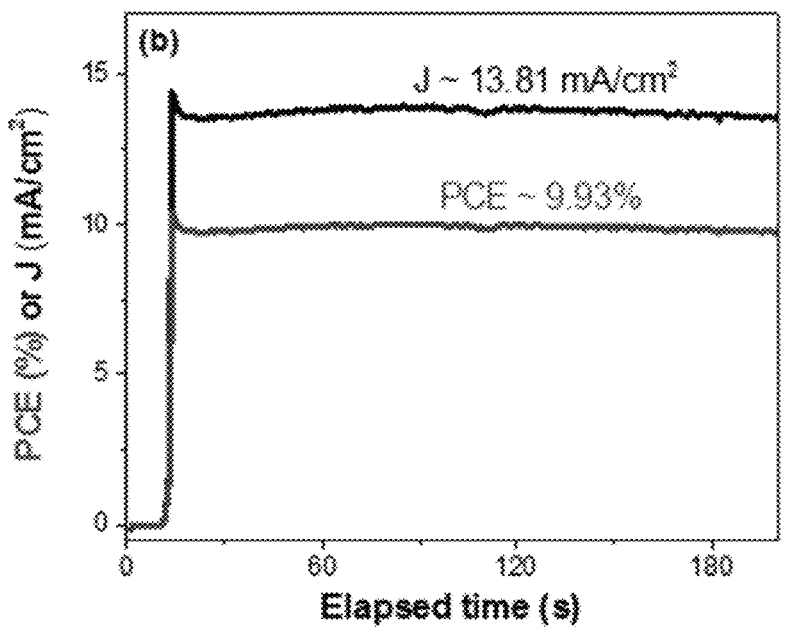
FIG. 3B shows stable output of current density (darker) and power conversion efficiency (lighter) at maximum power with respect to time for the device.

Photocurrent density-voltage (J-V) measurements were conducted to examine the photovoltaic performance of the 10% w/w PbSe doped $CH_3NH_3PbI_3$ device. The J-V curves of 10% w/w PbSe doped $CH_3NH_3PbI_3$ champion cell are illustrated in FIG. 3A. Power conversion efficiency (PCE) achieved on the champion cell through reverse scan was 10.4% and corresponding short-circuit current density, open-circuit voltage and fill factor were 16.73 $mA/cm^2$, 0.942 V and 0.662, respectively; whereas forward scan (low voltage to high voltage scan) led to an 8.6% conversion efficiency with corresponding short-circuit current density, open-circuit voltage and fill factors of 16.82 $mA/cm^2$, 0.911 V and 0.561, respectively; note that the difference of photovoltaic characteristics between two scan directions indicated a hysteresis during cell operation. As shown in FIG. 3B, stabilized output of 9.93% PCE and 13.81 $mA/cm^2$ current density was achieved, which echoes the photovoltaic parameters obtained from J-V scans, and validates the phenomenal solar cell performance realized on the 10% w/w PbSe-doped $CH_3NH_3PbI_3$ device. The data demonstrates that a chemical dopant with an electronic order higher than monovalent pseudohalides[4,30,55], can retain substantial photovoltaic properties in addition to the significantly enhanced chemical stabilities.

Figure 3C:
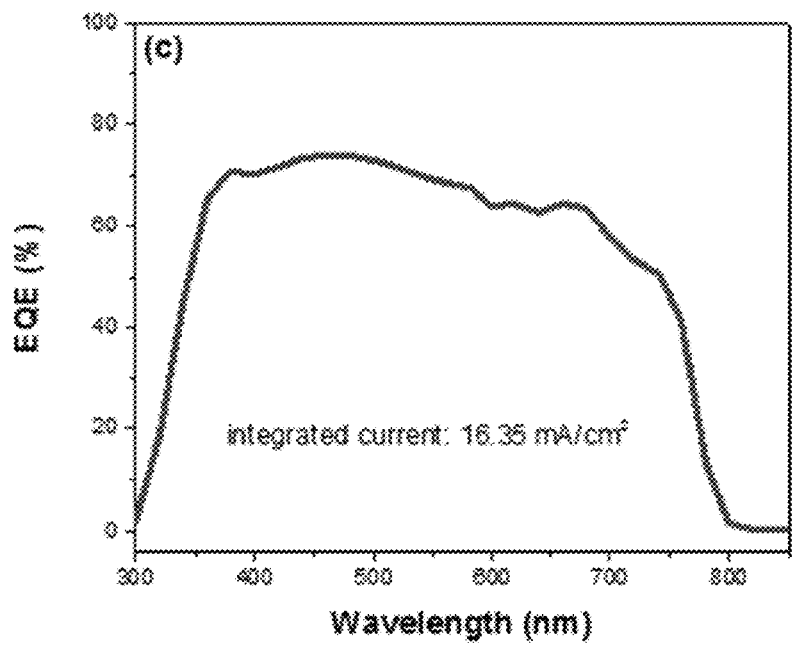
FIG. 3C shows IPCE spectrum of 10% w/w PbSe doped $CH_3NH_3PbI_3$ based thin film with an integrated area current density of 16.35 $mA/cm^2$.

Ideally, the doping approach should not excessively tamper with the perovskite structures of studied samples, for preserving the desired charge transport properties. To probe the optoelectronic profiles-photocarrier generation and collection processes happening in the PbSe doped $CH_3NH_3PbI_3$, the incident photon-to-current efficiency (IPCE) on the 10% w/w PbSe doped $CH_3NH_3PbI_3$ thin film was measured, as shown in FIG. 3C. The IPCE spectrum displays a high external quantum efficiencies that are ~60% in average between 375 nm and 750 nm, accounting for substantial charge generation and collection in the visible light region. When wavelength of incident photons exceeds 750 nm, external quantum efficiency starts to drastically decay, approaching zero starting from 800 nm, which corresponds to a ~1.5 eV bandgap, as being similar to IPCE spectra of undoped $CH_3NH_3PbI_3$ reported previously.[56,57] The comparable shapes of IPCE spectra of both doped and pristine $CH_3NH_3PbI_3$ films confirm the fact that perovskite photoelectric characteristics are largely unaffected with the presence of 10% w/w PbSe dopant in the structure.

REFERENCES

1. Chiang, C-H.; Wu, C-G. Nat. Photon. 2016, 10, 196-200.
2. Liu, D.; Kelly, T. L. Nat. Photon. 2014, 8, 133-138.
3. Noorden, R. V. Nature 2014, 513, 470.
4. Jiang, Q.; Rebollar, D.; Gong, J.; Piacentino, E. L.; Zheng, C.; Xu, T. Angew. Chem. Int. Ed. 2015, 54, 7617-7620.
5. Kazim, S.; Nazeeruddin, M. K.; Gratzel, M.; Ahmad, S. Angew. Chem. Int. Ed. 2014, 53, 2812-2824.
6. Miyata, A.; Mitioglu, A.; Plochocka, P.; Portugall, O.; Wang, J. T.-W.; Stranks, S. D.; Snaith, H. J.; Nicholas, R. J. Nat. Phys. 2015, 11, 582-587.
7. Chen, Y.; Yi, H. T.; Wu, X.; Haroldson, R.; Gartstein, Y. N.; Rodionov, Y. I.; Tikhonov, K. S.; Zakhidov, A.; Zhu, X.-Y.; Podzorov, V. Nat. Commun. 2016, 7, 12253.
8. Shi, D.; Adinolfi, V.; Comin, R.; Yuan, M.; Alarousu, E.; Buin, A.; Chen, Y.; Hoogland, S.; Rothenberger, A.; Katsiev, K.; Losovyj, Y.; Zhang, X.; Dowben, P. A.; Mohammed, O. F.; Sargent, E. H.; Bakr, O. M. Science 2015, 347, 519-522.
9. Wehrenfennig, C.; Eperon, G. E.; Johnston, M. B.; Snaith, H. J.; Herz, L. M. Adv. Mater. 2014, 26, 1584-1589.
10. Bi, Y.; Hutter, E. M.; Fang, Y.; Dong, Q.; Huang, J.; Savenije, T. J. J. Phys. Chem. Lett. 2016, 7, 923-928.
11. Burschka, J.; Pellet, N.; Moon, S-J.; Humphry-Baker, R.; Gao, P.; Nazeeruddin, M. K.; Grätzel, M. Nature 2013, 499, 316-319.
12. Im, J-H.; Jang, I-H.; Pellet, N.; Grätzel, M.; Park N-G. Nat. Nanotech. 2014, 9, 927-932.
13. Kaltenbrunner, M.; Adam, G.; Glowacki, E. D.; Drack, M.; Schwödiauer, R.; Leonat, L.; Apaydin, D. H.; Groiss, H.; Scharber, M. C.; White, M. S.; Sariciftci, N. S.; Bauer, S. Nat. Mater. 2015, 14, 1032-1039.
14. Green, M. A.; Ho-Baillie, A.; Snaith, H. J. Nat. Photon. 2014, 8, 506-514.
15. Jeon, N. J.; Noh, J. H.; Kim, Y. C.; Yang, W. S.; Ryu, S.; Seok, S. I. Nat. Mater. 2014, 13, 897-903.
16. Nie, W.; Tsai, H.; Asadpour, R.; Blancon, J-C.; Neukirch, A. J.; Gupta, G.; Crochet, J. J.; Chhowalla, M.; Tretiak, S.; Alam, M. A.; Wang, H-L.; Mohite, A. D. Science 2015, 347, 522-525.
17. Chen, W.; Wu, Y.; Yue, Y.; Liu, J.; Zhang, W.; Yang, X.; Chen, H.; Bi, E.; Ashraful, I.; Grätzel, M.; Han, L. Science 2015, 350, 944-948.
18. Noh, J. H.; Im, S. H.; Heo, J. H.; Mandal, T. N.; Seok, S. I. Nano Lett. 2013, 13, 1764-1769.
19. Zhu, H.; Fu, Y.; Meng, F.; Wu, X.; Gong, Z.; Ding, Q.; Gustafsson, M. V.; Trinh, M. T.; Jin, S.; Zhu, X-Y. Nat. Mater. 2015, 14, 636-642.
20. Fu, Y.; Zhu, H.; Schrader, A. W.; Liang, D.; Ding, Q.; Joshi, P.; Hwang, L.; Zhu, X-Y.; Jin, S. Nano Lett. 2016, 16, 1000-1008.
21. Fu, Y.; Zhu, H.; Stoumpos, C. C.; Ding, Q.; Wang, J.; Kanatzidis, M. G.; Zhu, X.; Jin, S. ACS Nano 2016, 10, 7963-7972.
22. Frost, J. M.; Butler, K. T.; Brivio, F.; Hendon, C. H.; van Schilfgaarde, M.; Walsh, A. Nano Lett. 2014, 14, 2584-2590.
23. Leguy, A. M. A.; Frost, J. M.; McMahon, A. P.; Sakai, V. G.; Kockelmann, W.; Law, C.; Li, X.; Foglia, F.; Walsh, A.; O'Regan, B. C.; Nelson, J.; Cabral, J. T.; Barnes, P. R. F. Nat. Commun. 2015, 6, 7124.
24. You, J.; Meng, L.; Song, T-B.; Guo, T-F.; Yang, Y.; Chang, W-H.; Hong, Z.; Chen, H.; Zhou, H.; Chen, Q.; Liu, Y.; De Marco, N.; Yang, Y. Nat. Nanotech. 2016, 11, 75-81.
25. Meloni, S.; Moehl, T.; Tress, W.; Franckevičius, M.; Saliba, M.; Lee, Y. H.; Gao, P.; Nazeeruddin, M. K.; Zakeeruddin, S. M.; Rothlisberger, U.; Graetzel, M. Nat. Commun. 2016, 7, 10334.
26. Frost, J. M.; Butler, K. T.; Walsh, A. APL Mater. 2014, 2, 081506.
27. Gratzel, M. Nat. Mater. 2014, 13, 838-842.
28. Li, X.; Dar, M. I.; Yi, C.; Luo, J.; Tschumi, M.; Zakeeruddin, S. M.; Nazeeruddin, M. K.; Han, H.; Grätzel, M. Nat. Chem. 2015, 7, 703-711.
29. Binek, A.; Hanusch, F. C.; Docampo, P.; Bein, T. J. Phys. Chem. Lett. 2015, 6, 1249-1253.
30. Tai, Q.; You, P.; Sang, H.; Liu, Z.; Hu, C.; Chan, H. L. W.; Yan, F. Nat. Commun. 2016, 7, 11105.
31. Cao, D. H.; Stoumpos, C. C.; Farha, O. K.; Hupp, J. T.; Kanatzidis, M. G. J. Am. Chem. Soc. 2015, 137, 7843-7850.
32. Daub, M.; Hillebrecht, H. Angew. Chem. Int. Ed. 2015, 54, 11016-11017.
33. Tsai, H.; Nie, W.; Blancon, J.-C.; Stoumpos, C. C.; Asadpour, R.; Harutyunyan, B.; Neukirch, A. J.; Verduzco, R.; Crochet, J. J.; Tretiak, S.; Pedesseau, L.; Even, J.; Alam, M. A.; Gupta, G.; Lou, J.; Ajayan, P. M.; Bedzyk, M. J.; Kanatzidis, M. G.; Mohite, A. D. Nature 2016, 536, 312-316.
34. Xiao, Z.; Meng, W.; Saparov, B.; Duan, H-S.; Wang, C.; Feng, C.; Liao, W.; Ke, W.; Zhao, D.; Wang, J.; Mitzi, D. B.; Yan, Y. J. Phys. Chem. Lett. 2016, 7, 1213-1218.
35. Ogomi, Y.; Morita, A.; Tsukamoto, S.; Saitho, T.; Fujikawa, N.; Shen, Q.; Toyoda, T.; Yoshino, K.; Pandey, S. S.; Ma, T.; Hayase, S. J. Phys. Chem. Lett. 2014, 5, 1004-1011.
36. Chen, Q.; De Marco, N.; Yang, Y.; Song, T-B.; Chen, C-C.; Zhao, H.; Hong, Z.; Zhou, H.; Yang, Y. Nano Today 2015, 10, 355-396.
37. Sutter-Fella, C. M.; Li, Y.; Amani, M.; Ager, J. W.; Toma, F. M.; Yablonovitch, E.; Sharp, I. D.; Javey, A. Nano Lett. 2016, 16, 800-806.
38. Yang, M.; Zhang, T.; Schulz, P.; Li, Z.; Li, G.; Kim, D. H.; Guo, N.; Berry, J. J.; Zhu, K.; Zhao, Y. Nat. Commun. 2016, 7, 12305.
39. Zhao, Y.; Zhu, K. J. Am. Chem. Soc. 2014, 136, 12241-12244.
40. Kong, L.; Liu, G.; Gong, J.; Hu, Q.; Schaller, R. D.; Dera, P.; Zhang, D.; Liu, Z.; Yang, W.; Zhu, K.; Tang, Y.; Wang, C.; Wei, S.-H.; Xu, T.; Mao, H.-k. Proc. Natl. Acad. Sci. U.S.A. 2016, 113, 8910-8915.
41. Evers, W. H.; Schins, J. M.; Aerts, M.; Kulkarni, A.; Capiod, P.; Berthe, M.; Grandidier, B.; Delerue, C.; van der Zant, H. S. J.; van Overbeek, C.; Peters, J. L.; Vanmaekelbergh, D.; Siebbeles, L. D. A. Nat. Commun. 2015, 6, 8195.
42. Miller, E. M.; Kroupa, D. M.; Zhang, J.; Schulz, P.; Marshall, A. R.; Kahn, A.; Lany, S.; Luther, J. M.; Beard, M. C.; Perkins, C. L.; van de Lagemaat, J. ACS Nano 2016, 10, 3302-3311.
43. Ekuma, C. E.; Singh, D. J.; Moreno, J.; Jarrell, M. Phys. Rev. B 2012, 85, 085205.

44. Zhang, N.; Neo, D. C. J.; Tazawa, Y.; Li, X.; Assender, H. E.; Compton, R. G.; Watt, A. A. R. ACS Appl. Mater. Interfaces 2016, Article ASAP, DOI: 10.1021/acsami.6b01018.

45. Svane, A.; Christensen, N. E.; Cardona, M.; Chantis, A. N.; van Schilfgaarde, M.; Kotani, T. Phys. Rev. B 2010, 81, 245120.

46. Primera-Pedrozo, O.; Arslan, Z.; Rusulev, B.; Leszczynski, Nanoscale. 2012, 4, 1312-1320.

47. Heo, J. H.; Im, S. H.; Noh, J. H.; Mandal, T. N.; Lim, C.-S.; Chang, J. A.; Lee, Y. H.; Kim, H.-j.; Sarkar, A.; Nazeeruddin, M. K.; Grätzel, M.; Seok, S. I. Nat. Photon. 2013, 7, 486-491.

48. Eperon, G. E.; Burlakov, V. M.; Docampo, P.; Goriely, A.; Snaith, H. J. Adv. Funct. Mater. 2014, 24, 151-157.

49. Lee, J-H.; Bristowe, N. C.; Bristowe, P. D.; Cheetham, A. K. Chem. Commun. 2015, 51, 6434-6437.

50. Ong, K. P.; Goh, T. W.; Xu, Q.; Huan, A. J. Phys. Chem. A 2015, 119, 11033-11038.

51. Stoumpos, C. C.; Malliakas, C. D.; Kanatzidis, M. G. Inorg. Chem. 2013, 52, 9019-9038.

52. Navas, J.; Sánchez-Coronilla, A.; Gallardo, J. J.; Hernández, N. C.; Piñero, J. C.; Alcántara, R.; Fernández-Lorenzo, C.; De los Santos, D. M.; Aguilar, T.; Martín-Calleja, J. Nanoscale 2015, 7, 6216-6229.

53. Li, Z.; Yang, M.; Park, J-S.; Wei, S-H.; Berry, J. J.; Zhu, K. Chem. Mater. 2016, 28, 284-292.

54. Aguiar, J. A.; Wozny, S.; Alkurd, N. R.; Yang, M.; Kovarik, L.; Holesinger, T. G.; Al-Jassim, M.; Zhu, K.; Zhou, W.; Berry, J. J. ACS Energy Lett. 2016, 1, 155-161.

55. Kim, M. K.; Jeon, T.; Park, H. I.; Lee, J. M.; Nam, S. A.; Kim, S. O. CrystEngComm 2016, 18, 6090-6095.

56. Gong, J.; Yang, M.; Ma, X.; Schaller, R. D.; Liu, G.; Kong, L.; Yang, Y.; Beard, M. C.; Lesslie, M.; Dai, Y.; Huang, B.; Zhu, K.; Xu, T. J. Phys. Chem. Lett. 2016, 7, 2879-2887.

57. Yang, M.; Zhou, Y.; Zeng, Y.; Jiang, C-S.; Padture, N. P.; Zhu, K. Adv. Mater. 2015, 27, 6363-6370.

58. Glaser, T.; Müller, C.; Sendner, M.; Krekeler, C.; Semonin, O. E.; Hull, T. D.; Yaffe, O.; Owen, J. S.; Kowalsky, W.; Pucci, A.; Lovrinčić, R. J. Phys. Chem. Lett. 2015, 6, 2913-2918.

59. Flender, O.; Klein, J. R.; Lenzer, T.; Oum, K. Phys. Chem. Chem. Phys. 2015, 17, 19238-19246.

60. Fornaro, T.; Burini, D.; Biczysko, M.; Barone, V. J. Phys. Chem. A 2015, 119, 4224-4236.

61. Al-Adhami, L.; Millen, D. J. Nature 1966, 211, 1291.

62. Yang, J-H.; Yin, W-J.; Park, J-S.; Wei, S-H. J. Mater. Chem. A 2016, 4, 13105-13112.

63. Yang, T. Y.; Gregori, G.; Pellet, N.; Gratzel, M.; Maier, J. Angew Chem. Int. Ed. 2015, 54, 7905-7910.

64. Yuan, Y.; Wang, Q.; Shao, Y.; Lu, H.; Li, T.; Gruverman, A.; Huang, J. Adv. Energy Mater. 2016, 6, 1501803.

65. Liu, M.; Johnston, M. B.; Snaith, H. J. Efficient Planar Heterojunction Perovskite Solar Cells by Vapour Deposition. Nature 2013, 501, 395-398.

66. Burschka, J.; Pellet, N.; Moon, S. J.; Humphry-Baker, R.; Gao, P.; Nazeeruddin, M. K.; Gratzel, M. Sequential Deposition as a Route to High-Performance Perovskite-Sensitized Solar Cells. Nature 2013, 499, 316-320.

67. Kazim, S.; Nazeeruddin, M. K.; Gratzel, M.; Ahmad, S. Perovskite as Light Harvester: A Game Changer in Photovoltaics. Angew. Chem., Int. Ed. 2014, 53, 2812-2824.

68. Stranks, S. D.; Eperon, G. E.; Grancini, G.; Menelaou, C.; Alcocer, M. J.; Leijtens, T.; Herz, L. M.; Petrozza, A.; Snaith, H. J. Electron-Hole Diffusion Lengths Exceeding 1 Micrometer in an Organometal Trihalide Perovskite Absorber. Science 2013, 342, 341-344.

69. Leijtens, T.; Eperon, G. E.; Pathak, S.; Abate, A.; Lee, M. M.; Snaith, H. J. Overcoming Ultraviolet Light Instability of Sensitized $TiO_2$ with Meso-Superstructured Organometal Tri-Halide Perovskite Solar Cells. Nat. Commun. 2013, 4, 2885.

70. Hao, F.; Stoumpos, C. C.; Cao, D. H.; Chang, R. P. H.; Kanatzidis, M. G. Lead-Free Solid-State Organic-Inorganic Halide Perovskite Solar Cells. Nat. Photonics 2014, 8, 489-494.

71. Qin, P.; Tanaka, S.; Ito, S.; Tetreault, N.; Manabe, K.; Nishino, H.; Nazeeruddin, M. K.; Gratzel, M. Inorganic Hole Conductor-Based Lead Halide Perovskite Solar Cells with 12.4% Conversion Efficiency. Nat. Commun. 2014, 5, 3834.

72. Christians, J. A.; Fung, R. C.; Kamat, P. V. An Inorganic Hole Conductor for Organo-Lead Halide Perovskite Solar Cells. Improved Hole Conductivity with Copper Iodide. J. Am. Chem. Soc. 2014, 136, 758-764.

73. Li, H.; Fu, K.; Hagfeldt, A.; Gratzel, M.; Mhaisalkar, S. G.; Grimsdale, A. C. A Simple 3,4-Ethylenedioxythiophene Based Hole-Transporting Material for Perovskite Solar Cells. Angew. Chem., Int. Ed. 2014, 53, 4085-4088.

74. Zhu, Z.; Ma, J.; Wang, Z.; Mu, C.; Fan, Z.; Du, L.; Bai, Y.; Fan, L.; Yan, H.; Phillips, D. L.; et al. Efficiency Enhancement of Perovskite Solar Cells through Fast Electron Extraction: The Role of Graphene Quantum Dots. J. Am. Chem. Soc. 2014, 136, 3760-3763.

75. Ku, Z.; Rong, Y.; Xu, M.; Liu, T.; Han, H. Full Printable Processed Mesoscopic $CH_3NH_3PbI_3$/$TiO_2$ Heterojunction Solar Cells with Carbon Counter Electrode. Sci. Rep. 2013, 3, 3132.

76. Lide, D. R. Handbook on Chemistry and Physics, 88th ed.; CRC: Boca Raton, F L, 2008; p 2640.

77. Feng, X.; Zhu, K.; Frank, A. J.; Grimes, C. A.; Mallouk, T. E. Rapid Charge Transport in Dye-Sensitized Solar Cells Made from Vertically Aligned Single-Crystal Rutile $TiO_2$ Nanowires. Angew. Chem., Int. Ed. 2012, 51, 2727-2730.

78. Etgar, L.; Gao, P.; Xue, Z.; Peng, Q.; Chandiran, A. K.; Liu, B.; Nazeeruddin, M. K.; Gratzel, M. Mesoscopic $CH_3NH_3PbI_3$/$TiO_2$ Heterojunction Solar Cells. J. Am. Chem. Soc. 2012, 134, 17396-17399.

89. Zhao, Y. X.; Zhu, K. Charge Transport and Recombination in Perovskite $CH_3NH_3PbI_3$ Sensitized $TiO_2$ Solar Cells. J. Phys. Chem. Lett. 2013, 4, 2880-2884.

90. Snaith, H. J.; Abate, A.; Ball, J. M.; Eperon, G. E.; Leijtens, T.; Noel, N. K.; Stranks, S. D.; Wang, J. T. W.; Wojciechowski, K.; Zhang, W. Anomalous Hysteresis in Perovskite Solar Cells. J. Phys. Chem. Lett. 2014, 5, 1511-1515.

91. Dualeh, A.; Moehl, T.; Tetreault, N.; Teuscher, J.; Gao, P.; Nazeeruddin, M. K.; Gratzel, M. Impedance Spectroscopic Analysis of Lead Iodide Perovskite-Sensitized Solid-State Solar Cells. ACS Nano 2014, 8, 362-373.

92. Green, M. A. Solar Cells: Operating Principles, Technology and System Applications; Holonyak, N., Jr., Ed.; Prentice-Hall, Inc.: Englewood Cliffs, N J, 1982; pp 96-97.

93. Jiang, Q.; Sheng, X.; Li, Y.; Feng, X.; Xu, T. Rutile $TiO_2$ Nanowires Perovskite Solar Cells. Chem. Commun. 2014, DOI: 10.1039/C4CC07367C.

94. O'Regan, B. C.; Bakker, K.; Kroeze, J.; Smit, H.; Sommeling, P.; Durrant, J. R. Measuring Charge Transport from Transient Photovoltage Rise Times. A New Tool to Investigate Electron Transport in Nanoparticle Films. J. Phys. Chem. B 2006, 110, 17155-17160.

95. Qinglong Jiang, Xia Sheng, Bing Shi, Xinjian Feng, and Tao Xu J., Nickel-Cathoded Perovskite Solar Cells, Phys. Chem. C 2014, 118, 25878-25883, supplemental information.

96. Q. Jiang, X. Sheng, Y. Li, X. Feng, T. Xu, *Chem Commun (Camb)* 2014, 50, 14720-14723.

97. G. D. Niu, W. Z. Li, F. Q. Meng, L. D. Wang, H. P. Dong, Y. Qiu, *J Mater Chem A* 2014, 2, 705-710.

98. A. Abate, M. Saliba, D. J. Hollman, S. D. Stranks, K. Wojciechowski, R. Avolio, G. Grancini, A. Petrozza, H. J. Snaith, *Nano Lett* 2014, 14, 3247-3254.

99. B. D. S. Jinli Yang, Dianyi Liu, Timothy L. Kelly, *Acs Nano* 2015, 9, 1955-1963.

100. Q. Chen, H. P. Zhou, T. B. Song, S. Luo, Z. R. Hong, H. S. Duan, L. T. Dou, Y. S. Liu, Y. Yang, *Nano Lett* 2014, 14, 4158-4163.

101. B. P. Byung-wook Park, Torbjörn Gustafsson, Kári Sveinbjörnsson, Anders Hagfeldt, Erik M. J. Johansson, Gerrit Boschloo, *Chem. Mater.* 2014, 26, 4466-4471.

102. T. Baikie, Y. N. Fang, J. M. Kadro, M. Schreyer, F. X. Wei, S. G. Mhaisalkar, M. Graetzel, T. J. White, *J Mater Chem A* 2013, 1, 5628-5641.

103. Freitag, Marina, et al., Dye-sensitized solar cells for efficient power generation under ambient lighting. Nature Photonics 2017, 10.1038.

104. Saparov, Bayrammurad, et al., Organic-Inorganic perovskites: structural versatility for functional materials design. Chemical Review 2016, 116, 4558-4596

105. Stoumpos, Constantinos C., et al., Ruddlesden-Popper hybrid lead iodide perovskite 2D homologous semiconductors. Chem Mater. 2016, 28, 2852-2867

106. Tsai, Hsinhan, et al., High-efficiency two dimensional Ruddlesden-Popper perovskite solar cells. Nature August 2016, vol 536, pg 312

107. Daub, Michael, et al., Synthesis, single crystal structure and characterization of $(CH_3NH_3)_2Pb(SCN)_2I_2$. Angew Chem. Int. Ed. 2015, 54, 11016-11017

What is claimed is:

1. A light-harvesting material, comprising: a perovskite absorber doped with a metal chalcogenide, wherein
   the perovskite absorber has the formula $ABX_3$,
   A is selected from the group consisting of methyl ammonium, formamidinium and mixtures thereof,
   B is lead,
   X is I, and
   the metal of the metal chalcogenide is lead,
   the chalcogenide of the metal chalcogenide is selected from the group consisting of S, Se and mixtures thereof, and
   the metal chalcogenide is present in an amount of 5 to 10 percent by weight.

2. The light-harvesting material of claim 1, wherein
   A is methyl ammonium,
   and
   the chalcogenide of the metal chalcogenide is Se.

3. A photovoltaic device, comprising:
   (1) a first conductive layer,
   (2) optionally an electron blocking layer, on the first conductive layer,
   (3) a semiconductor layer, on the first conductive layer,
   (4) a light-harvesting material, on the semiconductor layer,
   (5) a hole transport material, on the light-harvesting material, and
   (6) a second conductive layer, on the hole transport material,
   wherein the light-harvesting material comprises a perovskite absorber doped with a metal chalcogenide,
   the perovskite absorber has the formula $ABX_3$,
   A is selected from the group consisting of methyl ammonium, formamidinium and mixtures thereof,
   B is lead,
   X is I, and
   the metal of the metal chalcogenide is lead,
   the chalcogenide of the metal chalcogenide is selected from the group consisting of S, Se and mixtures thereof, and
   the metal chalcogenide is present in an amount of 5 to 10 percent by weight.

4. The photovoltaic device of claim 3, wherein
   A is methyl ammonium,
   and
   the chalcogenide of the metal chalcogenide is Se.

5. The photovoltaic device of claim of claim 3, further comprising the electron blocking layer.

6. The photovoltaic device of claim 3, wherein the first conductive layer is transparent.

7. The photovoltaic device of claim 6, wherein the first conductive layer comprises at least one transparent conductor selected from the group consisting of indium-tin oxide, fluorinated tin oxide and aluminum-zinc oxide.

8. A method of making the light-harvesting material of claim 1, comprising:
   forming a solution comprising:
     a first component selected from the group consisting of methyl ammonium, formamidinium and mixtures thereof,
     a second component of lead,
     a third component of I, and
     a fourth component selected from the group consisting of S, Se, and mixtures thereof, and
   forming the light-harvesting material from the solution.

9. The method of claim 8, further comprising depositing the light-harvesting material on a semiconductor layer by spin-coating.

10. A method of forming the photovoltaic device of claim 3, comprising:
    forming the first conductive layer, and optionally the blocking layer on the first conductive layer;
    forming the semiconductor layer, on the first conductive layer;
    applying the light-harvesting material, onto the semiconductor layer;
    forming the hole transport layer, on the semiconductor layer; and
    forming the second conductive layer, on the hole transport layer.

11. The method of claim 10, wherein forming the semiconductor layer comprises a solvothermal method.

12. The method of claim 10, wherein forming the second conductive layer comprises sputtering or evaporation.

13. The method of claim 10, wherein applying the light-harvesting material comprises spin coating.

* * * * *